United States Patent
Onishi et al.

(10) Patent No.: US 6,388,146 B1
(45) Date of Patent: May 14, 2002

(54) POLYMERIZABLE COMPOUND, POLYMERIZABLE RESIN COMPOSITION, CURED POLYMER AND LIQUID CRYSTAL DISPLAY DEVICE

(75) Inventors: Noriaki Onishi, Nara; Aya Miyazaki, Tenri; Hoyo Mizobe, Soka; Masahiko Yoshida, Soka; Kenji Suzuki, Soka, all of (JP)

(73) Assignees: Sharp Kabushiki Kaisha; Kanto Kagaku Kabushiki Kaisha, both of Tokyo (JP)

( * ) Notice: Subject to any disclaimer, the term of this patent is extended or adjusted under 35 U.S.C. 154(b) by 0 days.

(21) Appl. No.: 09/237,915

(22) Filed: Jan. 27, 1999

(30) Foreign Application Priority Data

Jan. 28, 1998 (JP) ............................................. 10-016209

(51) Int. Cl.[7] ......................... C07C 19/08; C07C 17/02; C07C 17/00; C07C 49/105; C07C 49/115; C07C 49/76; C07C 41/00; C07C 15/40; C07C 1/207; C07C 69/96

(52) U.S. Cl. ..................... 570/128; 570/123; 570/124; 570/125; 570/126; 570/127; 568/325; 568/326; 568/335; 568/626; 568/630; 568/659; 568/661; 568/663; 585/435; 585/436; 558/270

(58) Field of Search ................................ 570/127, 126, 570/125, 124, 123, 128; 585/435, 436; 568/325, 326, 335, 626, 630, 659, 661, 663; 558/270

(56) References Cited

FOREIGN PATENT DOCUMENTS

| JP | 7-120728 A | | 5/1995 |
|---|---|---|---|
| JP | WO 97/34855 | * | 9/1997 |

* cited by examiner

Primary Examiner—Samuel Barts
Assistant Examiner—Elvis O. Price
(74) Attorney, Agent, or Firm—Nixon & Vanderhye

(57) ABSTRACT

The polymerizable compound of this invention is represented by general formula (I):

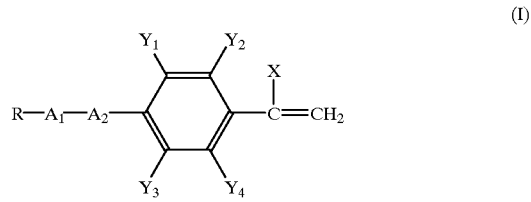

(I)

where R is H, R', R'O, R'COO, or R'OCO, R' is a linear or branched alkyl group or alkenyl group having 1 to about 15 carbon atoms, $A_1$ and $A_2$ are independently a cyclohexane ring or a benzene ring which may include a substituent represented by formula (II) below; X is H or $CH_3$; and $Y_1$, $Y_2$, $Y_3$, and $Y_4$ are independently H, F, Cl, $CH_3$, $CH_3O$, $CF_3$, or $CF_3O$ wherein at least two of $Y_1$, $Y_2$, $Y_3$, and $Y_4$ are H and, if both $A_1$ and $A_2$ are cyclohexane rings, at least one of $Y_1$, $Y_2$, $Y_3$, and $Y_4$ is not H:

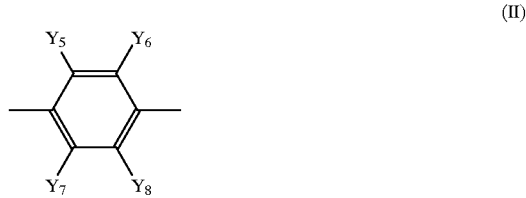

(II)

where $Y_5$, $Y_6$, $Y_7$, and $Y_8$ are independently H, F, Cl, $CH_3$, $CH_3O$, $CF_3$, or $CF_3O$, at least two of $Y_5$, $Y_6$, $Y_7$, and $Y_8$ are H.

5 Claims, 11 Drawing Sheets

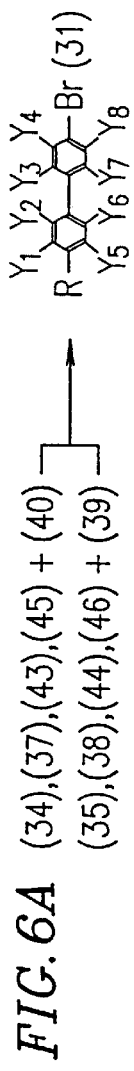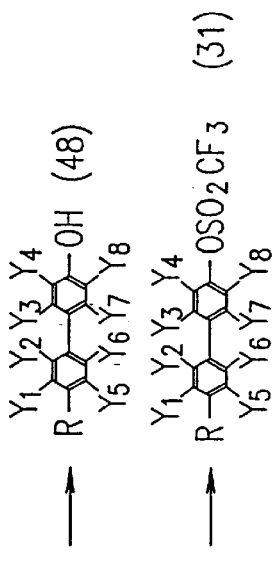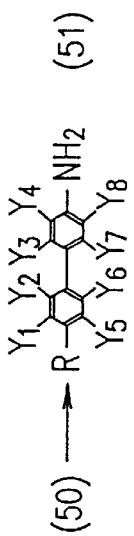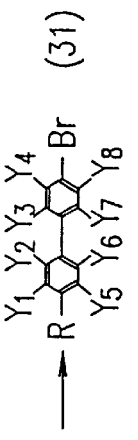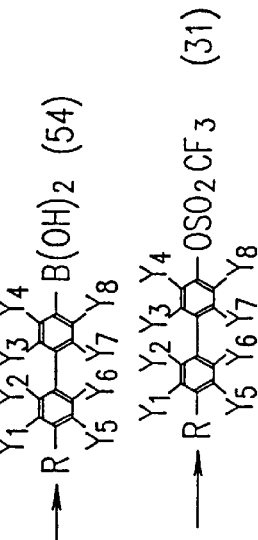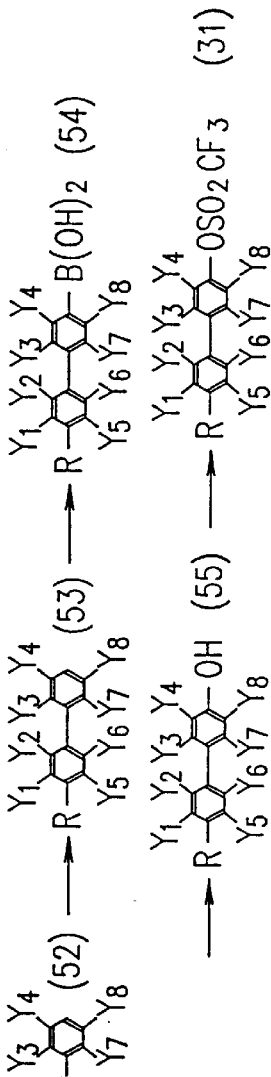
FIG. 6A
FIG. 6B
FIG. 6C
FIG. 6D (a)

PRIOR ART

POLYMERIZABLE COMPOUND, POLYMERIZABLE RESIN COMPOSITION, CURED POLYMER AND LIQUID CRYSTAL DISPLAY DEVICE

BACKGROUND OF THE INVENTION

1. Field of the Invention

The present invention relates to a liquid crystal display device used by a single person or a plurality of people, such as a wordprocessor, a personal computer, or a mobile information terminal, a polymerizable compound suitable for such a liquid crystal display device, a polymerizable resin composition containing such a compound, and a cured polymer formed from such a composition. In this specification, a liquid crystal display device will be referred to as an "LCD device".

2. Description of the Related Art

Conventionally, the following LCD devices using a composite of a liquid crystal material and a polymer are known.

Japanese National Phase PCT Laid-Open Publication No. 58-501631, for example, describes a polymer dispersed liquid crystal display device (hereinafter, referred to as a "PDLC display device"). The PDLC display device includes liquid crystal domains each surrounded by a polymer matrix. When no voltage is applied to the liquid crystal material, the refractive indices of the liquid crystal material and the polymer are not matched, resulting in a scattered state. When a voltage is applied to the liquid crystal material, the refractive index of the liquid crystal material changes so as to be matched with that of the polymer, resulting in a transparent state.

Japanese National Phase PCT Laid-Open Publication No. 61-502128, for example, describes an LCD device in which a mixture of the liquid crystal material and a photopolymerizable resin is irradiated with ultraviolet light, resulting in three-dimensional phase separation into a liquid crystal material and a polymer.

The above-described LCD devices perform display by electrically controlling the liquid crystal material so that it is in the scattered state or the transparent state.

Japanese Laid-Open Publication No. 1-269922 describes the following method. A mixture of a liquid crystal material and a photopolymerizable resin is subjected to a first exposure to ultraviolet light through a photomask. After the photomask is removed, the mixture is subjected to a second exposure with ultraviolet light, so that an area covered by the photomask during the first exposure is irradiated with ultraviolet light. Thus, areas having different display characteristics are formed. An LCD device produced by this method basically performs in a scattered mode.

Japanese Laid-Open Publication No. 5-257135 describes an LCD device produced by the following method. An alignment layer having an alignment restricting force is provided on each of two substrates. Into a gap between the two substrates, a mixture of a liquid crystal material and a photopolymerizable resin is injected. The mixture of the liquid crystal material and the photopolymerizable resin is irradiated with ultraviolet light through a photomask. The LCD device produced by this method is used for static driving, by which liquid crystal domains are patterned by a control performed outside the cell, utilizing that an area covered by the photomask and an area not covered by the photomask have different threshold characteristics.

As an attempt to improve the viewing angle characteristic of the LCD devices, use of a composite of a liquid crystal material and a polymer has been proposed. It is necessary that liquid crystal molecules are oriented in at least three directions in a pixel area in order to improve the orientation state of the liquid crystal molecules and thus the viewing angle characteristic.

With reference to FIGS. 8A and 8B, the viewing angle characteristic of a wide viewing angle mode LCD device are described.

FIG. 8A schematically shows the relationship between a change in the orientation of liquid crystal molecules and the viewing angle characteristic in accordance with application of a voltage regarding a wide viewing angle mode LCD device 10. FIG. 8B schematically shows such relationship regarding a conventional twisted nematic(TN) mode LCD device. In both FIGS. 8A and 8B, part (a) illustrates the state where no voltage is applied, part (b) illustrates an intermediate state where a voltage is applied to a certain degree less than full, and part (c) illustrates the state where the voltage is applied to a full degree.

As shown in FIG. 8A, the wide viewing angle mode LCD device 10 includes substrates 1 and 2. A liquid crystal layer interposed between the substrates 1 and 2 includes a polymer wall 7 surrounding a liquid crystal domain 8. Liquid crystal molecules 9 included in the liquid crystal domain 8 are oriented symmetrically with respect to an axis 6. Accordingly, in the intermediate state shown in part (b), the apparent refractive indices of the liquid crystal molecules 9 when seen in directions A and B are averaged to be equal. As a result, the viewing angle characteristic is improved compared to the TN mode shown in FIG. 8B.

In the conventional TN mode LCD device shown in FIG. 8B, the liquid crystal molecules have only one orientation direction in the intermediate state shown in part (b). Accordingly, display characteristics such as the levels of brightness and the apparent refractive indices of the liquid crystal molecules when seen in directions A and B are different. As a result, the viewing angle characteristic is inferior to that of the LCD device 10.

The following LCD devices are disclosed as wide viewing angle mode LCD devices.

Japanese Laid-Open Publication Nos. 4-338923 and 4-212928 disclose a wide viewing angle mode LCD apparatus produced by combining the above-described PDLC display device and polarizers having polarizing axes perpendicular to each other.

Japanese Laid-Open Publication. No. 5-27242 discloses a method for improving the viewing angle characteristic of a non-scattering mode LCD device using polarizers. According to the method, a mixture of a liquid crystal material and a photopolymerizable resin is phase-separated, thereby forming a liquid crystal layer formed of a composite of the liquid crystal material and a polymer. Due to such a method, the orientation of liquid crystal domains becomes random by the resultant polymer. In other words, the liquid crystal molecules in different domains rise in different orientation directions when a voltage is applied. As a result, the transmittance of the liquid crystal molecules becomes equal when seen in a plurality of directions, thus improving the viewing angle characteristic in a half-tone display.

The applicant of the present invention discloses the following LCD device in Japanese Laid-Open Publication No. 6-301015. The LCD device is produced by controlling the amount of light using a photomask or the like during photopolymerization, so that the liquid crystal molecules are oriented in an all-direction state (axially symmetrical orientation) in a pixel area, and that the area which is not covered with the photomask forms a polymer wall mainly composed of a photocurable resin.

In the above-described LCD device, disclination is generated at the interface between the polymer wall and the liquid crystal domain due to a reverse tilt of the liquid crystal molecules in the liquid crystal domain. Such disclination is exhibited as a bright line on the display and thus the display characteristics degrade in a black state.

In order to overcome the problem of generation of disclination when a voltage is applied, the applicant of the present invention discloses, in Japanese Laid-Open Publication No. 7-120728, a technique where a polymerizable compound having a liquid crystal-like structure is added to a mixture of a liquid crystal composition and a photocurable resin.

By using the above polymerizable compound, however, the following two problems arise.

First, the pretilt of the liquid crystal molecules in the liquid crystal domain becomes large in a normally-white mode, reducing the brightness of the display when no voltage is applied.

Secondly, the response speed, the threshold characteristic and sharpness in the voltage vs. transmittance characteristic, and the like decrease due to the interaction between the polymer and the liquid crystal material in the composite layer and between the polymer wall and the liquid crystal domain at the interface thereof, and the like.

In the LCD device having an improved viewing angle characteristic, such as the device disclosed in Japanese Laid-Open Publication No. 6-301015, it is difficult to (1) control the orientation of liquid crystal molecules so that the liquid crystal molecules are oriented omnidirectionally, and (2) prevent a reduction of contrast caused by depolarization of light which is scattered at the interface of the liquid crystal material and the polymer.

In order to suppress the light scattering at the interface of the liquid crystal material and the polymer, the occurrence of such an interface in a pixel area may be reduced. In order to reduce the occurrence of the interface, the size and the position of liquid crystal droplets produced in a three-dimensional polymer matrix must be controlled. In conventional methods, however, such control is extremely difficult.

In order to solve the above problems, it is important that the above polymerizable compound used for suppressing generation of disclination should be suitably selected so that the response speed and the voltage vs. transmittance characteristic can be prevented from decreasing. It would be advantageous, also, if at least one liquid crystal droplet can be formed in one pixel area.

In other words, in order to realize an LCD device where a conventional liquid crystal mode is pseudo-solidified, the above problems of controlling the orientation of liquid crystal molecules and controlling the scattering intensity at the interface must be solved preferably simultaneously or at least individually. It is therefore very important to obtain a polymerizable compound which can solve both of these problems.

In the case of using a polymerizable compound having a liquid crystal-like structure described above, if such a compound has a comparatively high polymerization, it is likely to disturb the orientation of liquid crystal molecules and provide an excessively strong memory effect at the interface of the liquid crystal material and the polymer, causing a printing afterimage phenomenon and the like. Providing a suitable polymerizable compound is therefore a critical problem.

SUMMARY OF THE INVENTION

The polymerizable compound of this invention is represented by general formula (I):

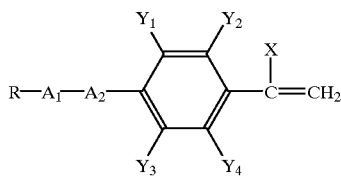

(I)

where R is H, R', R'O, R'COO, or R'OCO, R' is a linear or branched alkyl group or alkenyl group having 1 to about 15 carbon atoms; $A_1$ and $A_2$ are independently a cyclohexane ring or a benzene ring which may include a substituent represented by formula (II) below; X is H or $_3$; and $Y_1$, $Y_2$, $Y_3$, and $Y_4$ are independently H, F, Cl, $CH_3$, $CH_3O$, $CF_3$, or $CF_3O$ wherein at least two of $Y_1$, $Y_2$, $Y_3$, and $Y_4$ are H and, if both $A_1$ and $A_2$ are cyclohexane rings, at least one of $Y_1$, $Y_2$, $Y_3$, and $Y_4$ is not H:

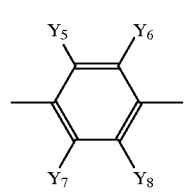

(II)

where $Y_5$, $Y_6$, $Y_7$, and $Y_8$ are independently H, F, Cl, $CH_3$, $CH_3O$, $CF_3$, or $CF_3O$, at least two of $Y_5$, $Y_6$, $Y_7$, and $Y_8$ are H.

In one embodiment of the invention, in general formula (I) $A_1$ is a cyclohexane ring and $A_2$ is a benzene ring.

In another embodiment of the invention, in general formula (I) both $A_1$ and $A_2$ are cyclohexane rings.

Alternatively, the polymerizable compound of this invention is represented by general formula (III):

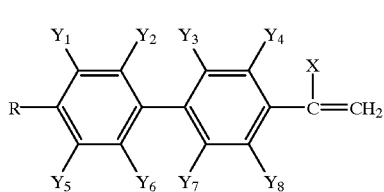

(III)

where R is H, F, or a linear or branched alkyl group or alkoxy group having 1 to 15 carbon atoms of which an arbitrary hydrogen atom may be substituted by a fluorine atom; $Y_1$, $Y_2$, $Y_3$, $Y_4$, $Y_5$, $Y_6$, $Y_7$, and $Y_8$ are independently H or F; X is H or $CH_3$ wherein at least one of $Y_1$, $Y_2$, $Y_3$, $Y_4$, $Y_5$, $Y_6$, $Y_7$, and $Y_8$ is F if R is a linear alkyl group of which an arbitrary hydrogen atom is not substituted by a fluorine atom.

According to one aspect of the invention, a polymerizable resin composition is provided, which includes a polymerizable resin material containing the polymerizable compound described above and a photoinitiator mixed with each other.

According to another aspect of the invention, a cured polymer is provided, which is obtained by polymerizing the polymerizable resin composition described above.

According to still another aspect of the invention, a liquid crystal display device is provided. The liquid crystal display device includes a polymer wall and liquid crystal domains surrounded by the polymer wall, the polymer wall and the liquid crystal domains being interposed between a pair of substrates, wherein the polymer wall includes the cured polymer described above.

In one embodiment of the invention, the polymerizable resin composition includes the polymerizable compound in an amount equal to or more than about 3 wt. % and equal to or less than about 40 wt. %.

Alternatively, the liquid crystal display device of this invention includes a polymer wall and liquid crystal domains surrounded by the polymer wall, the polymer wall and the liquid crystal domains being interposed between a pair of substrates, wherein at least part of an area of the polymer wall which is in contact with the liquid crystal domains includes the cured polymer described above.

In one embodiment of the invention, liquid crystal molecules in each of the liquid crystal domains are allowed to be oriented in an axially symmetric state.

In another embodiment of the invention, the liquid crystal domains are arranged regularly.

In still another embodiment of the invention, the liquid crystal display device further includes a liquid crystal alignment layer provided on a surface of at least one of the pair of substrates, the surface facing the liquid crystal domains.

In still another embodiment of the invention, liquid crystal molecules in the liquid crystal domains are oriented in one of a twisted nematic manner, a super twisted nematic manner, an electrically controlled birefringence manner, and a surface stabilized ferroelectric liquid crystal manner.

In still another embodiment of the invention, the liquid crystal domains are each provided for one pixel area which is a minimum unit for display.

Arbitrary hydrogen means one or more hydrogen atoms on the alkyl or alkoxy group is randomly substituted by a fluorine atom.

Thus, the polymerizable compound according to the present invention is a compound having a liquid crystal-like structure and a polymerizable functional group in molecules. The existence of a liquid crystal-like structure in molecules serves to stabilize the orientation of liquid crystal molecules in liquid crystal domains. The polymerizable functional group is a styrene or -methylstyrene group which has an excellent selectivity during the polymerization reaction and a high polymerization rate. This allows for a reduction of the anchoring strength of the liquid crystal molecules by adjusting the interaction between the liquid crystal molecules and the polymer at the interface thereof.

Thus, the invention described herein makes possible the advantages of providing (1) a liquid crystal display device which does not disturb the orientation state of liquid crystal molecules, minimizes a decrease of the response speed and the voltage vs. transmittance characteristics, has an improved contrast ratio, and suppresses an occurrence of a printing afterimage phenomenon even in a fixed display, (2) a polymerizable compound suitable for such a liquid crystal display device, (3) a polymerizable resin composition containing such a compound, and (4) a cured polymer formed from such a composition.

These and other advantages of the present invention will become apparent to those skilled in the art upon reading and understanding the following detailed description with reference to the accompanying figures.

BRIEF DESCRIPTION OF THE DRAWINGS

FIGS. 6A, 6B, 6C, and 6D are views illustrating synthesis processes for the reaction intermediate for the polymerizable compound according to one aspect of the present invention;

DESCRIPTION OF THE PREFERRED EMBODIMENTS

Figure 1:
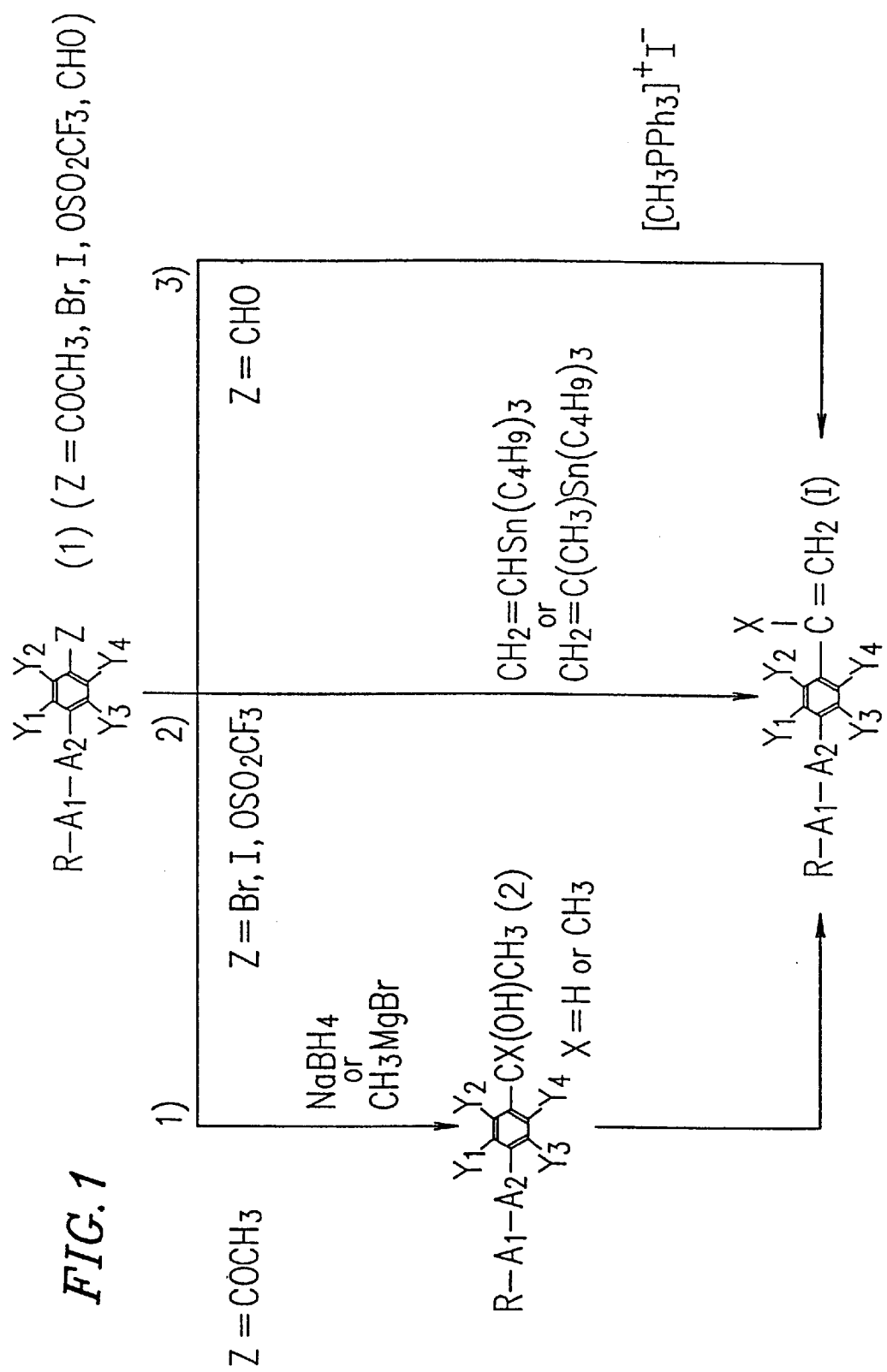
FIG. 1 is a view illustration synthesis process for a polymerizable compound according to one aspect of the present invention.

Hereinbelow, the present invention will be described by way of examples. As used herein, a liquid crystal layer "having liquid crystal domains surrounded by a polymer wall or a wall structure" refers to a liquid crystal layer having a structure where liquid crystal molecules in the liquid crystal layer are separated from other liquid crystal molecules by the existence of a polymer, forming a plurality of liquid crystal domains, including: a liquid crystal layer having liquid crystal domains each completely surrounded by or covered with a polymer wall; a liquid crystal layer having liquid crystal domains each partitioned by a column-like or wall-like polymer; and a liquid crystal layer having liquid crystal domains each partitioned by a three-dimensional mesh structure composed of a polymer.

(Polymerizable Compound)

[Structure]

The polymerizable compound according to the present invention is a compound including a methogen group having a structure similar to that of a liquid crystal compound and a polymerizable functional group coupled to the methogen group, and having a single functional structure having one polymerization group in a molecule. One of the most important features of the polymerizable compound of the present invention is that the polymerizable functional group is a styrene or -methylstyrene group as represented by general formula (I) or (III) above.

[Features of the Styrene and -Methylstyrene Polymerizable Compound]

Styrene resins are generally characterized as having low polymerization reactivity compared with acrylate resins and methacrylate resins. More specifically, in an optical radical polymerization reaction, a free radical in a reaction intermediate of a styrene functional group is more stabilized and lives longer, compared with that of an acrylate functional group, due to the non-localized effect of electrons, reducing the polymerization reactivity. The low polymerization reactivity tends to improve the selectivity of polymerization reaction involving styrene type compounds. This increases the polymerization conversion and thus facilitates more uniform polymerization.

The above feature is more significant when a double-bond carbon is -methylated because a free radical of the reaction intermediate is even more stabilized.

The prior art problems described above can be minimized or solved effectively by adding one or more kinds of styrene or -methylstyrene polymerizable compounds having the above feature to a polymerizable resin at a fixed ratio.

The following effects can be obtained by using the polymerizable compound according to the present invention.

1) When a mixture of a liquid crystal material and a polymerizable resin is used for an LCD device of a display mode which utilizes the alignment regulating force of an alignment film provided on a substrate, a polymerization layer composed of a composite of the polymer and the liquid crystal material is formed between the alignment film, and liquid crystal domains. This generally tends to reduce the alignment regulating force of the alignment film on liquid crystal molecules of the liquid crystal domains.

If the polymerizable compound having a liquid crystal-like structure according to the present invention is included in the polymerization layer, the polymerizable compound can activate the alignment regulating force of the alignment film on the liquid crystal molecules of the liquid crystal domains, thereby stabilizing the orientation state of the liquid crystal molecules.

2) When the liquid crystal display molecules are oriented in an axially symmetrical state in each liquid crystal domain, disclination lines are normally generated along a periphery of the liquid crystal domain due to a reverse tilt of the liquid crystal molecules when a voltage is applied.

By using the polymerization compound according to the present invention, the liquid crystal molecules can be provided with a pretilt at the surface of the substrate. This suppresses the generation of disclination lines.

3) The above two effects can be obtained from the polymerizable compound proposed by Japanese Laid-Open Publication No. 7-120728, which is hereby incorporated by reference. As described above, however, the conventional polymerizable compound has problems caused by the decrease of the response speed, the decrease of the threshold characteristic and sharpness in the volt age vs. transmittance characteristics, and the like due to the interaction between the liquid crystal domains and the polymer wall at the interface thereof, and the like. Thus, the conventional polymerizable compound still has problems to be solved in the electrooptical characteristics thereof.

The polymerizable compound having a styrene or -methylstyrene functional group according to the present invention can adjust the interaction between the liquid crystal molecules and the polymer wall at the interface thereof, and thereby reduce the anchoring strength of the liquid crystal molecules. By using such a polymerizable compound, problems caused by the decrease of the response speed, the decrease of the threshold characteristic and sharpness in the voltage vs. transmittance characteristic, and the like, as well as a printing afterim age phenomenon caused by an excessively strong memory effect at the interface, can be suppressed.

If $A_1$ is a cyclohexane ring and $A_2$ is a benzene ring in formula (I) above, the selectivity of polymerization reaction can be easily improved.

If both $A_1$ and $A_2$ are cyclohexane rings in formula (I) above, the refractive index of the resultant polymer is small. This makes it easy to match the refractive index between the polymer and the liquid crystal material and thus obtain a high-contrast display.

If a fluorine atom is introduced into a portion of the liquid crystal-like core structure, the orientation state of the liquid crystal molecules in the liquid crystal domains can be further stabilized. More specifically, by fluorinating the methogen group, fluorine atoms easily orient themselves on the surface of the polymer wall. This reduces the surface energy of the polymer wall, thereby reducing the anchoring strength of the liquid crystal molecules. In this way, the memory effect can be adjusted.

(Synthesis Process)

The polymerizable compound according to the present invention can be synthesized in the following manner. The synthesis processes described hereinbelow are merely illustrative; not intended to restrict the present invention.

[Synthesis of a Polymerizable Compound Represented by Formula (I)]

The polymerizable compound represented by formula (I) above can be obtained via a reaction intermediate (1) along the synthesis processes shown in FIG. 1, for example.

1) When Z=COCH$_3$

If X=H, the reaction intermediate (1) is reduced with sodium borohydride to obtain a reaction intermediate (2). If X=CH$_3$, the reaction intermediate (1) is reacted with methylmagnesium bromide to obtain the reaction intermediate (2).

The reaction intermediate (2) is dehydrated using toluenesulfonic acid to obtain the target polymerizable compound (I) according to the present invention.

2) When Z=Br, I, OSO$_2$CF$_3$

If X=H, the reaction intermediate (1) is reacted with tributylvinyltin in the presence of a palladium catalyst to obtain the target polymerizable compound (I) according to the present invention. If X=CH$_3$, the reaction intermediate (1) is reacted with tributyl(1-methylvinyl) tin to obtain the target polymerizable compound (I) according to the present invention.

3) When Z=CHO

If X=H, the reaction intermediate (1) is subjected to Wittig reaction with methyl triphenylphosphonium iodide, to obtain the target polymerizable compound (I) according to the present invention.

Figure 2:
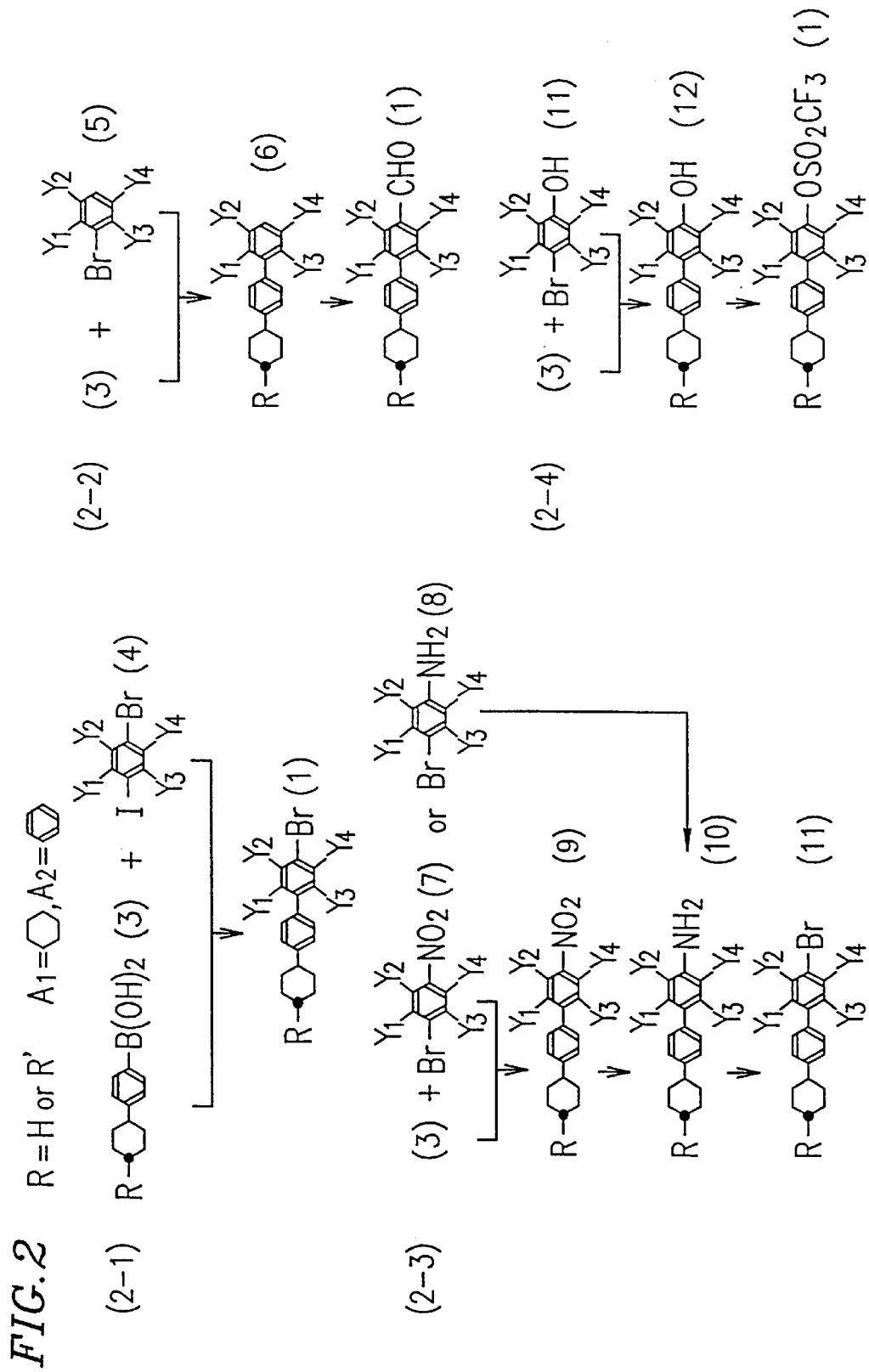
FIG. 2 is a view illustrating a synthesis process f or a reaction intermediate for the polymerizable compound according to one aspect of the present invention.
Figure 3:
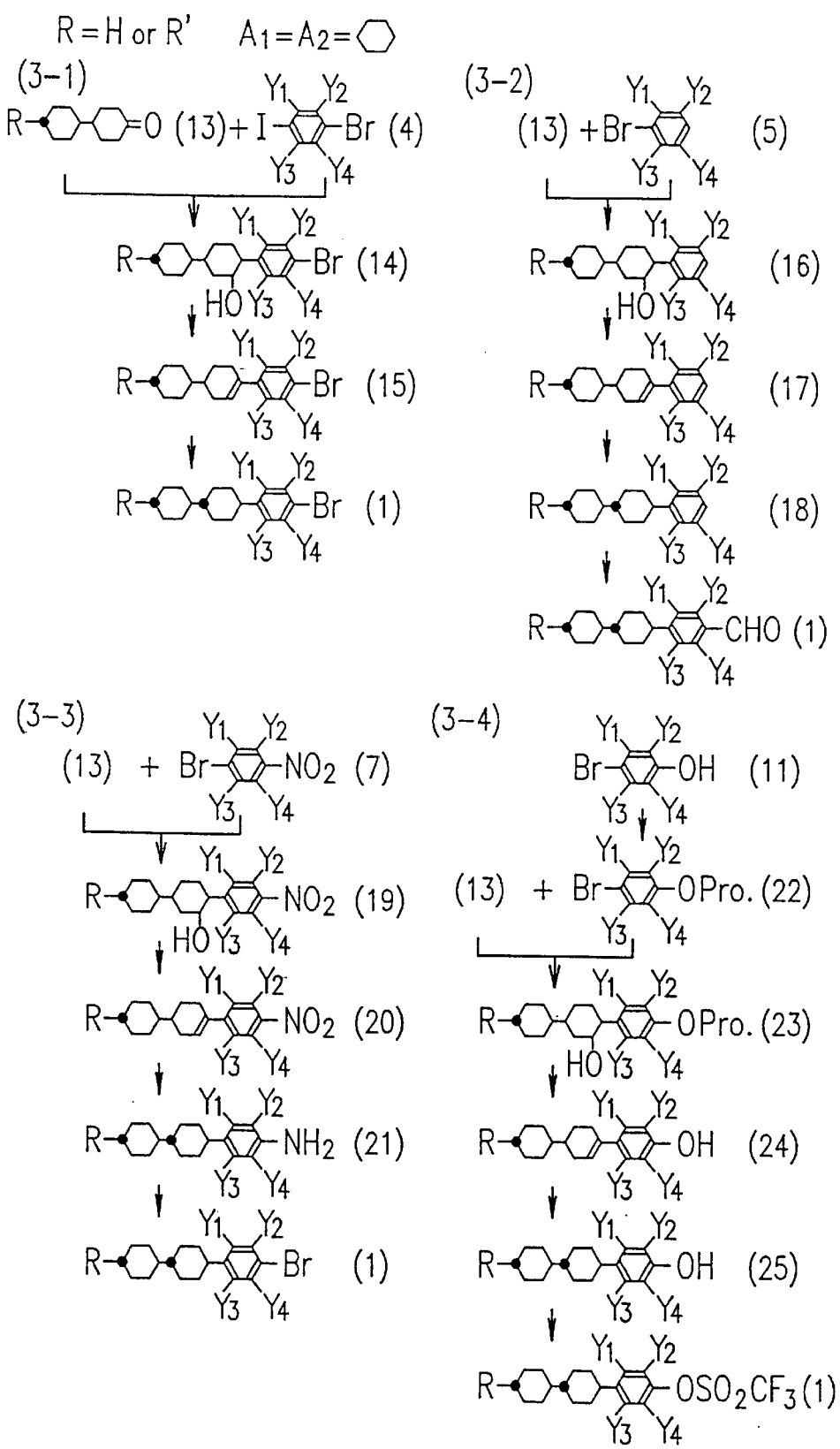
FIG. 3 is a view illustrating a synthesis process for the reaction intermediate for the polymerizable compound according to one aspect of the present invention.

The reaction intermediate (1) can be synthesized along synthesis processes shown in FIGS. 2 and 3, for example.

FIG. 2 illustrates synthesis processes for the reaction intermediated (1) when R=H or R', $A_1$ is a cyclohexane ring, and $A_2$ is a benzene ring.

(2-1) Trans-alkylcyclohexylphenylboronic acid (3) and a bromoiodobenzene compound (4) are coupled in the presence of a palladium catalyst, to obtain the reaction intermediate (1).

As the bromoiodobenzene compound (4), compounds such as those represented by:

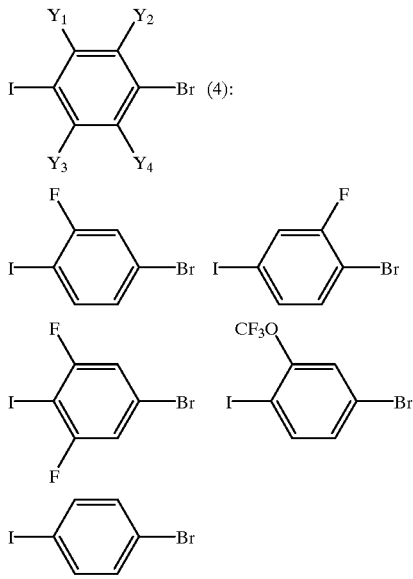

are commercially available.

(2-2) Trans-alkylcyclohexylphenylboronic acid (3) and a bromobenzene compound (5) are coupled in the presence of a palladium catalyst to obtain a compound (6), which is then reacted with dimethylformaldehyde in the presence of butyllithium, to obtain the reaction intermediate (1).

As the bromobenzene compound (5), compounds such as those represented by:

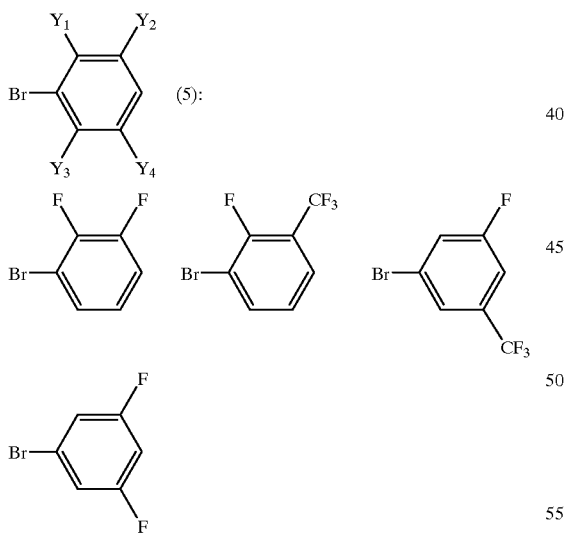

are commercially available.

(2-3) Trans-alkylcyclohexylphenylboronic acid (3) and a bromonitrobenzene compound (7) are coupled in the presence of a palladium catalyst to obtain a compound (9). The nitro group of the compound (9) is reduced to obtain a compound (10), which is then subjected to a Sandmeyer reaction, to obtain the reaction intermediate (1).

The compound (10) can also be obtained by a direct coupling reaction between alkylcyclohexylphenyl boronic acid (3) and a bromoaniline compound (8).

As the bromonitrobenzene compound (7), compounds such as those represented by:

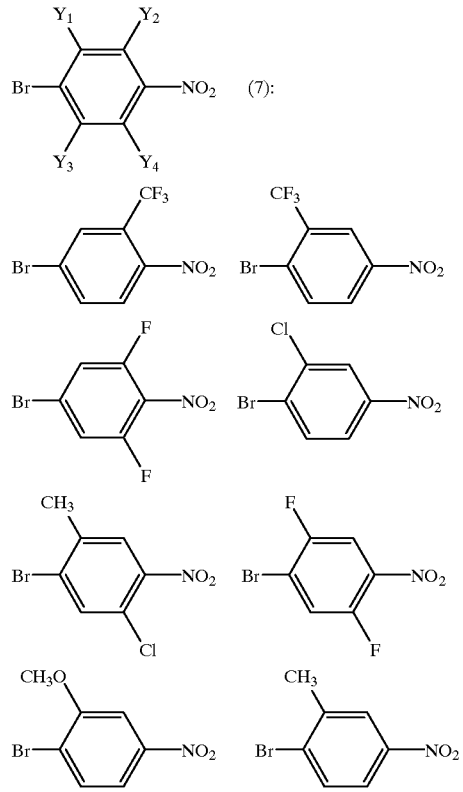

are commercially available..

As the bromoaniline compound (8), compounds such as those represented by:

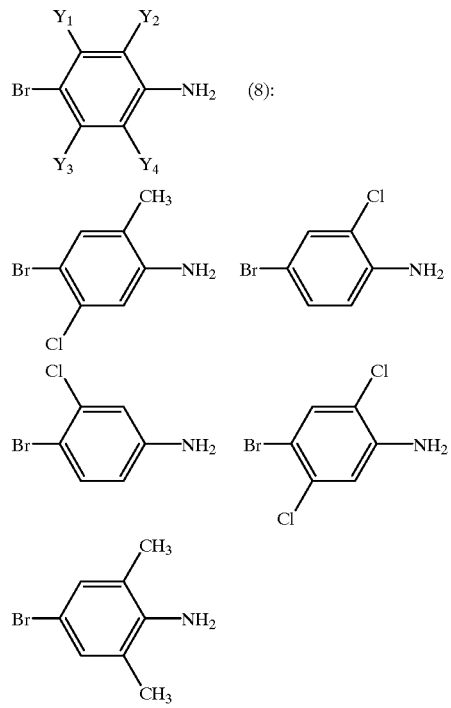

are commercially available.

(2-4) Trans-alkylcyclohexylphenylboronic acid (3) and a bromophenol compound (11) are coupled in the presence of a palladium catalyst to obtain a compound (12), which is then reacted with trifluoromethanesulfonic anhydride, to obtain the reaction intermediate (1).

The hydroxyl group of the bromophenol compound (11) may be pre-protected with a protecting group. After the coupling, the protecting group may be removed.

As the bromophenol compound (11), compounds such as those represented by:

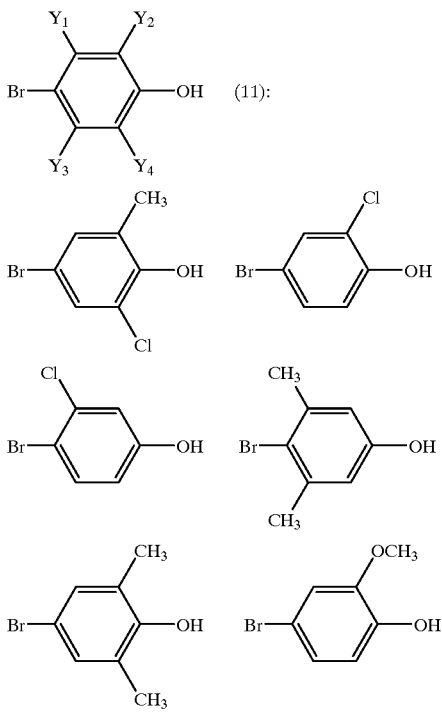

are commercially available.

FIG. 3 illustrates the synthesis processes for the reaction intermediate (1) when R=H or R', and both $A_1$ and $A_2$ are cyclohexane rings.

(3-1) A compound (13) and the bromoiodobenzene compound (4) are condensed in the presence of butyllithium to obtain a compound (14), which is then dehydrated using toluenesulfonic acid to obtain a compound (15). Thereafter, the compound (15) is hydrogenated in the presence of a platinum oxide catalyst, and a trans-form moiety of the compound (15) is isolated by recrystallization or column chromatography, to obtain the reaction intermediate (1).

(3-2) The compound (13) and the bromobenzene compound (5) are condensed in the presence of butyllithium to obtain a compound (16), which is then dehydrated using toluenesulfonic acid to obtain a compound (17). Thereafter, the compound (17) is hydrogenated in the presence of a Pd—C catalyst, and a trans-form moiety of the compound (17) is isolated by recrystallization or column chromatography, to obtain a compound (18). Thereafter the compound (18) is reacted with dimethylformaldehyde in the presence of butyllithium, to obtain the reaction intermediate (1).

(3-3) The compound (13) and the bromonitrobenzene compound (7) are condensed in the presence of butyllithium to obtain a compound (19), which is then dehydrated using toluenesulfonic acid to obtain a compound (20). Thereafter, the compound (20) is hydrogenated in the presence of a Pd—C catalyst or a platinum oxide catalyst, and a trans-form moiety is isolated by recrystallization or column chromatography, to obtain a compound (21). The compound (21) is then subjected to a Sandmeyer reaction, to obtain the reaction intermediate (1).

(3-4) The hydroxy group of the bromophenol compound (11) is protected with a methoxymethyl group to obtain a compound (22). The compounds (13) and (22) are condensed in the presence of butyllithium to obtain a compound (23), which is then dehydrated using toluenesulfonic acid. The protecting group is then removed to obtain a compound (24). Thereafter, the compound (24) is hydrogenated in the presence of a Pd—C catalyst or a platinum oxide catalyst, and a trans-form moiety is isolated by recrystallization or column chromatography, to obtain a compound (25). The compound (25) is then reacted with trifluoromethanesulfonic anhydride, to obtain the reaction intermediate (1).

Reaction intermediates other than the reaction intermediate (1) shown in FIGS. 2 and 3 can also be synthesized by selecting appropriate materials and performing reactions such as oxidation, reduction, substitution of a functional group, and coupling.

[Synthesis of Polymerizable Compound Represented by Formula (III) Above]

Figure 4:
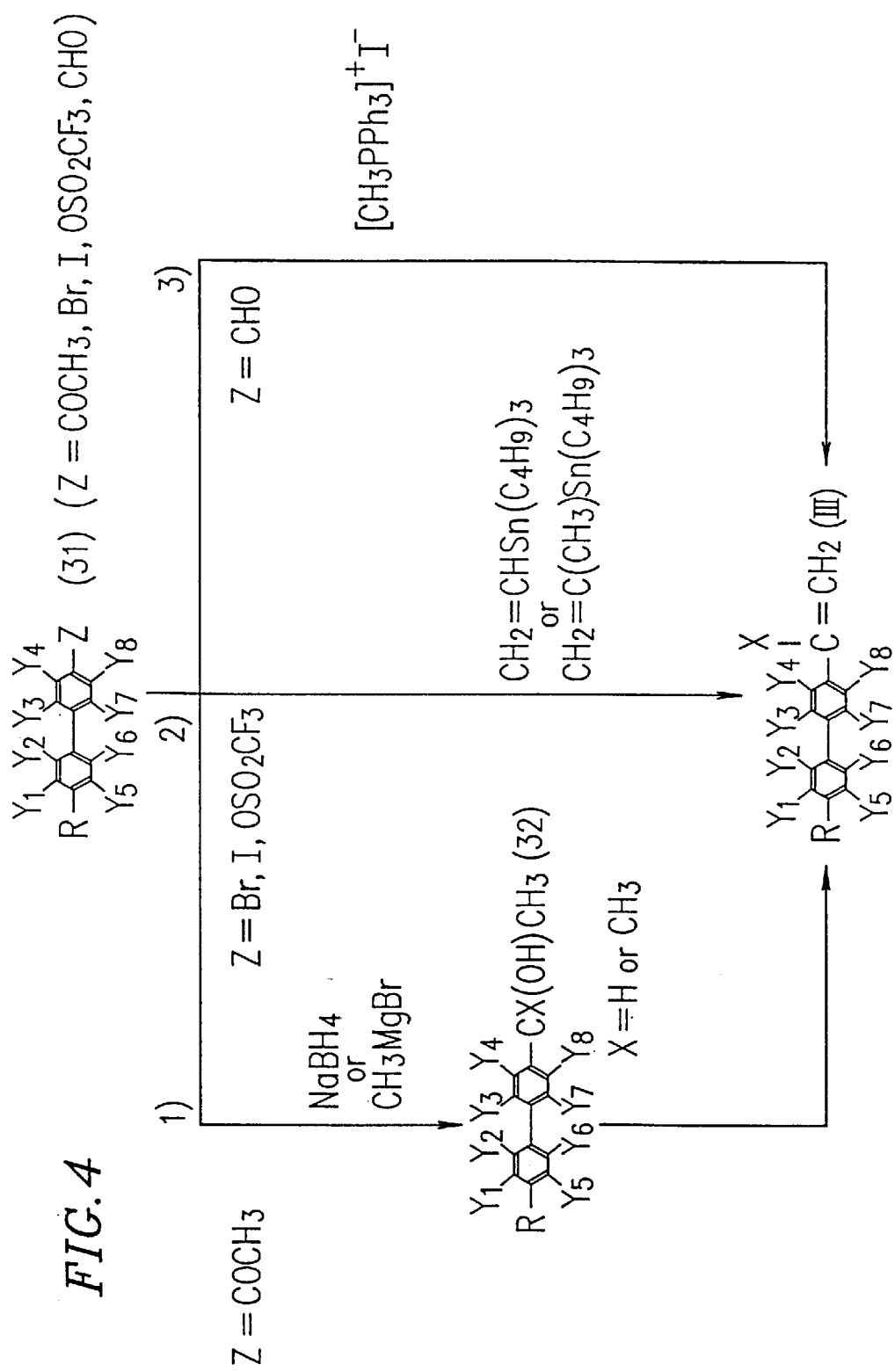
FIG. 4 is a view illustrating a synthesis process for a polymerizable compound according to one aspect of the present invention.

The polymerizable compound represented by formula (III) above can be obtained via a reaction intermediate (31) along the synthesis processes shown in FIG. 4, for example.

1) When $Z=COCH_3$

If X=H, the reaction intermediate (31) is reduced with sodium borohydride to obtain a reaction intermediate (32). If $X=CH_3$, the reaction intermediate (31) is reacted with methylmagnesium bromide to obtain the reaction intermediate (32).

The reaction intermediate (32) is dehydrated using toluenesulfonic acid to obtain the target polymerizable compound (III) according to the present invention.

2) When Z=Br, I, $OSO_2CF_3$

If X=H, the reaction intermediate (31) is reacted with tributylvinyltin in the presence of a palladium catalyst to obtain the target polymerizable compound (III) according to the present invention. If $X=CH_3$, the reaction intermediate (31) is reacted with tributyl(1-methylvinyl) tin to obtain the target polymerizable compound (III) according to the present invention.

3) When Z=CHO

If X=H, the reaction intermediate (31) is subjected to a Wittig reaction with methyl triphenylphosphonium iodide, to obtain the target polymerizable compound (III) according to the present invention.

Figure 5:
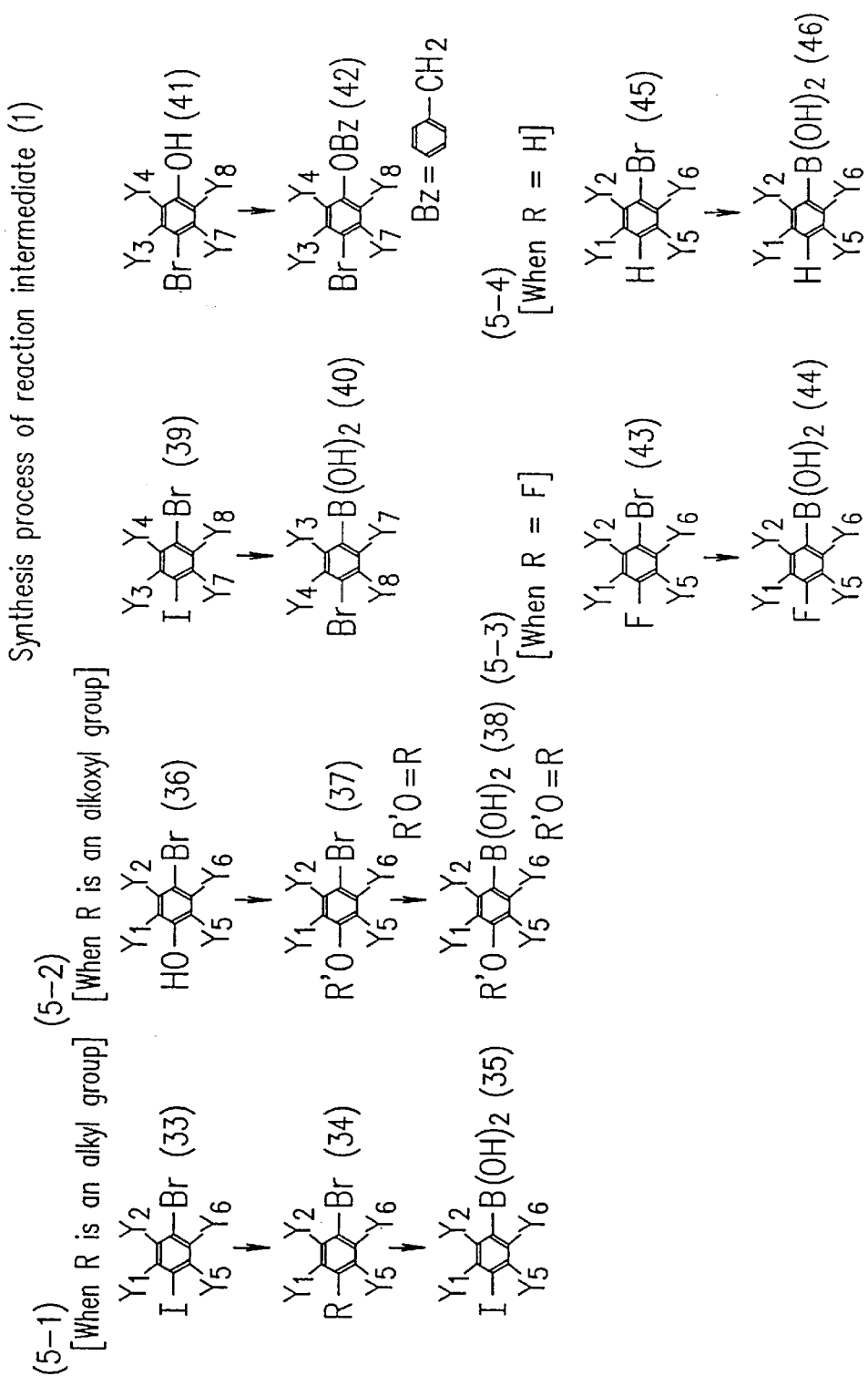
FIG. 5 is a view illustrating a synthesis process for a reaction intermediate for the polymerizable compound according to one aspect of the present invention.

The reaction intermediate (31) can be synthesized along synthesis processes shown in FIGS. 5 and 6, for example.

(5-1) When R is an alkyl group

A compound (33) is coupled with alkylmagnesium bromide (RMgBr) in the presence of a palladium catalyst, to obtain a-compound (34). If R is a perfluoroalkyl group, the compound (33) is coupled with perfluoroalkyl iodide in the presence of a copper catalyst, to obtain the compound (34). Thereafter, trimethyl borate is added to the compound (34) to hydrolyze the compound (34) under acidic conditions, thereby to obtain a compound (35).

The reaction intermediate (31) is obtained using the compound (34) or (35) in processes shown in FIGS. 6A to 6D as follows.

(a) A compound (39) is reacted with trimethyl borate in the presence of butyllithium to hydrolyze the compound (39), thereby to obtain a compound (40).

The compounds (34) and (40) or the compounds (35) and (39) are coupled in the presence of a palladium catalyst, to obtain the reaction intermediate (31).

As the compounds (33) and (39), compounds such as those represented by:

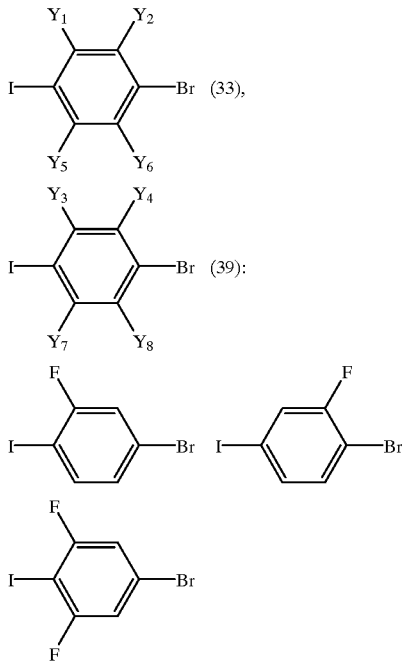

are commercially available.

(b) The hydroxyl group of a compound (41) is protected with a benzyl group to obtain a compound (42). The compound (42) is coupled with the compound (35) in the presence of a palladium catalyst, to obtain a compound (47). The protecting group is then removed using Pd—C and hydrogen gas to obtain a compound (48), which is reacted with trifluoromethanesulfonic anhydride, to obtain the reaction intermediate (31).

As the compound (41), compounds such as those represented by:

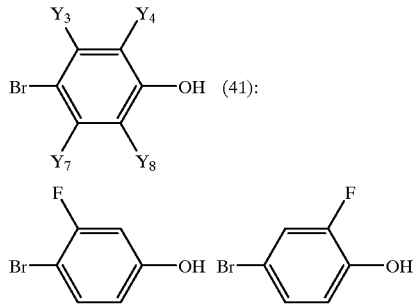

are commercially available.

(c) The compound (35) and a compound (49) are coupled in the presence of a palladium catalyst to obtain a compound (50). The nitro group of the compound (50) is reduced using Pd—C and hydrogen gas, to obtain a compound (51), which is then subjected to a Sandmeyer reaction to obtain the reaction intermediate (31).

As the compound (49), compounds such as those represented by:

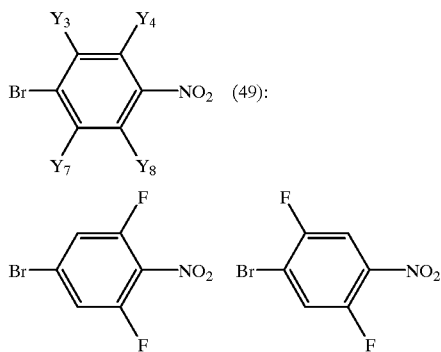

are commercially available.

(d) The compound (35) and a compound (52) are coupled in the presence of a palladium catalyst to obtain a compound (53). Trimethyl borate is added to the compound (53) in the presence of butyllithium to hydrolyze the compound (53) under acidic conditions, to obtain a compound (54). The compound (54) is then oxidized with hydrogen peroxide to obtain a compound (55), which is reacted with trifluoromethanesulfonic anhydride, to obtain the reaction intermediate (31).

As the compound (52), compounds such as those represented by:

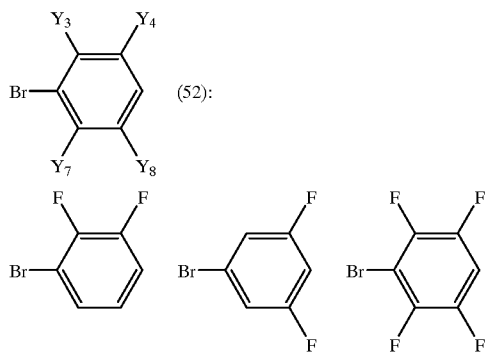

are commercially available.

(5-2) When R is an alkoxy group

A compound (36) is etherified with alkyl bromide (R'Br), alkyl tosylate (R'OTs), alkyl triflate (R'OTf), or the like, to obtain a compound (37). Trimethyl borate is added to the compound (37) in the presence of butyllithium to hydrolyze the compound (37) under acidic conditions, to obtain a compound (38).

Substantially the same operation as that in the case where R is an alkyl group described above is performed in this case, using the compound (37) in place of the compound (34) or the compound (38) in place of the compound (35), to obtain the reaction intermediate (31).

As the compound (36), compounds such as those represented by:

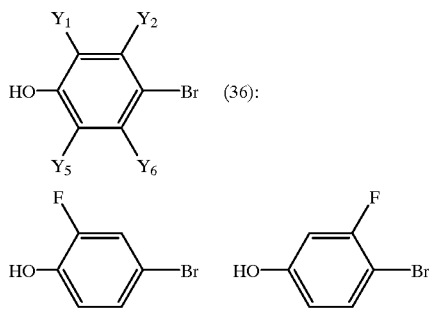

are commercially available.

(5-3) When R=F

Boric acid trimethyl ester is added to a compound (43) in the presence of butyllithium to hydrolyze the compound (43) under acidic conditions, to obtain a compound (44).

Substantially the same operation as that in the case where R is an alkyl group described above is performed in this case, using the compound (43) in place of the compound (34) or the compound (44) in place of the compound (35), to obtain the reaction intermediate (31).

As the compound (43), compounds such as those represented by:

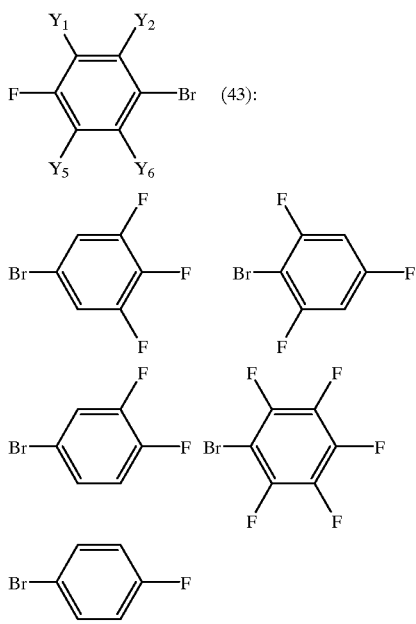

are commercially available.

(5-4) When R=H

Boric acid trimethyl ester is added to a compound (45) in the presence of butyllithium to hydrolyze the compound (45) under acidic conditions, to obtain a compound (46).

Substantially the same operation as that in the case where: R is an alkyl group described above is performed in this case, using the compound (45) in place of the compound (34) or the compound (46) in place of the compound (35), to obtain the reaction intermediate (31).

As the compound (45), compounds such as those represented by:

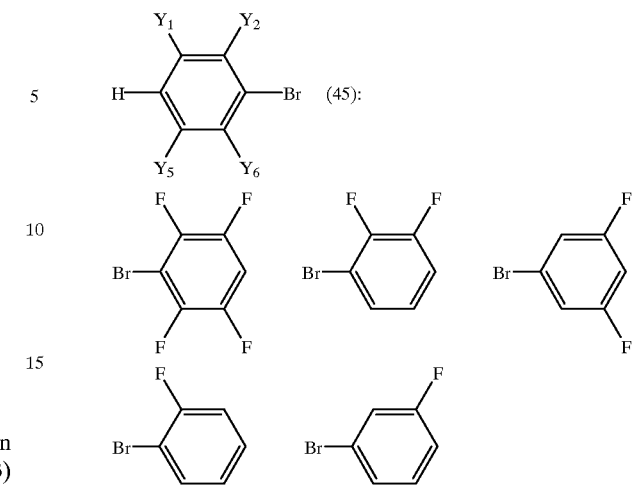

are commercially available.

Figure 7:
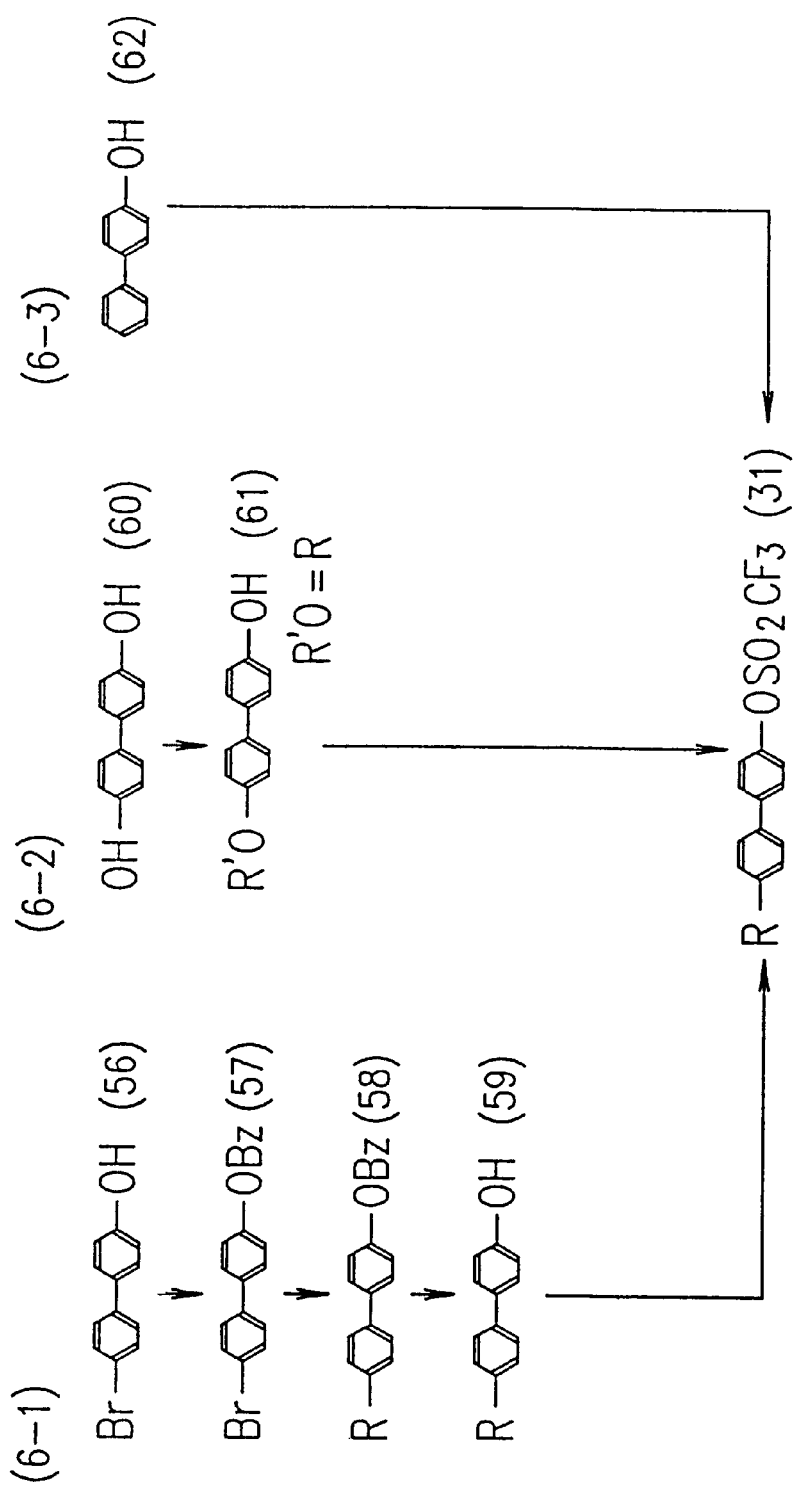
FIG. 7 is a view illustrating a synthesis process for the reaction intermediate for the polymerizable compound according to one aspect of the present invention.

If $Y_1=Y_3=Y_4=Y_5=Y_6=Y_7=Y_8=H$, the reaction intermediate (31) can be synthesized along synthesis processes shown in FIG. 7 as described below.

(6-1) When R is alkyl group

The hydroxy group of a compound (56) is protected with a benzyl group to obtain a compound (57). The compound (57) is coupled with alkylmagnesium bromide (RMgBr) in the presence of a palladium catalyst, to obtain the compound (58). If R is a perfluoroalkyl group, the compound (57) is coupled with perfluoroalkyl iodide in the presence of a copper catalyst, to obtain the compound (58).

Thereafter, the protecting group is removed using Pd—C and hydrogen gas to obtain a compound (59), which is reacted with trifluoromethanesulfonic anhydride, to obtain the reaction intermediate (31).

(6-2) When R is an alkoxy group

A compound (60) is etherified with alkyl bromide (R'Br), alkyl tosylate (R'OTs), alkyl triflate (R'OTf), or the like, to obtain a compound (61). The compound (61) is then reacted with trifluoromethanesulfonic anhydride, to obtain the reaction intermediate (31).

(6-3) When R=H

A compound (62) is reacted with trifluoromethanesulfonic anhydride to obtain the reaction intermediate (31).

(Polymerizable Resin Composition)

The polymerizable resin composition according to the present invention includes a polymerizable resin material containing at least one type of the polymerizable compound according to the present invention and a photoinitiator.

[Polymerizable Resin Material]

Selection of a photopolymerizable resin material is important since the photopolymerizable resin material is mixed with a liquid crystal material and finally constitutes a wall for supporting a pair of substrates and liquid crystal domains.

According to the present invention, in order to form a liquid crystal layer where liquid crystal domains are surrounded by a polymer wall, which is described hereinbelow, the polymerizable resin material having a polymerizable functional group preferably contains the polymerizable compound according to the present invention in an amount of about 3 wt. % or more and about 40 wt. % or less, and more preferably in an amount of about 5 wt. % or more and about 35 wt. % or less.

If the amount of the polymerizable compound according to the present invention is less than about 3 wt. %, the above effect is unlikely to be sufficiently exhibited. If it exceeds about 40 wt. %, the polymerization activity of the polymerizable resin material is extremely reduced thus failing to proceed efficiently. As a result, the effect of the polymerizable resin material of stabilizing the liquid crystal molecules in the liquid crystal domains is not sufficiently obtained.

Other usable materials having a polymerizable functional group contained in the polymerizable resin material include, for example, photocurable resin monomers. Photocurable resin monomers include, for example, acrylic acids or acrylates having a long-chain alkyl group of $C_3$ or more or aromatic group. Photocurable resin monomers further include isobutyl acrylate, stearyl acrylate, lauryl acrylate, isoamyl acrylate, n-butyl methacrylate, n-lauryl methacrylate, tridecyl methacrylate, 2-ethylhexyl acrylate, n-stearyl methacrylate, cyclohexyl methacrylate, benzyl methacrylate, and 2-phenoxyethyl methacrylate.

In order to improve the physical strength of the polymer, multi-functional resins having two or more functionalities, for example, the resins listed below are also usable: bisphenol A dimethacrylate, bisphenol A diacrylate, 1,4-butanediol methacrylate, 1,6-hexanediol dimethacrylate, trimethylolpropane triacrylate, and tetramethylolmethane tetraacrylate.

Resins produced by halogenation, specifically chlorinating or fluorinating the above-described monomers are also usable. Such resins include, for example, 2,2,3,4,4,4-hexafluorobutyl methacrylate, 2,2,3,4,4,4-hexachlorobutyl methacrylate, 2,2,3,3-tetrafluoropropyl methacrylate, 2,2,3,3-tetrachloropropyl methacrylate, perfluorooctylethyl methacrylate, perchlorooctylethyl methacrylate, perfluorooctylethyl acrylate, and perchlorooctylethyl acrylate.

The above-described photopolymerizable resin materials can be used independently or in combination of two or more thereof. The above-described monomers can be mixed with chlorinated or fluorinated polymers or oligomers, as necessary.

[Photoinitiator]

As the photoinitiator, general photopolymerization initiators, such as Irgacure 651, 184, 907, and Darocure 1173, 1116, 2956, can be used. A sensitizer which enables polymerization by visible light may be used for improving the retaining ratio of the photoinitiator.

(Cured Polymer)

The mixture of the polymerizable resin composition according to the present invention and a liquid crystal material is injected into a panel and irradiated with light, so as to obtain the liquid crystal layer where liquid crystal domains are surrounded by a polymer wall.

In particular, the polymerizable compound according to the present invention contains in molecules thereof a structure similar to that of liquid crystal molecules. The cured polymer obtained in the polymerization process has been confirmed to be very effective since an area of the cured polymer which is in direct contact with the liquid crystal material contributes to the improvement of orientation stability and chemical stability of the liquid crystal molecules.

The above mixture is usable as, for example, a panel seal resin used during production of the liquid crystal panel or after the liquid crystal material is injected.

(Liquid Crystal Domains)

[Liquid Crystal Material]

Usable liquid crystal materials are organic mixtures exhibiting a liquid crystal state at room temperature and the vicinity thereof, and include, for example, nematic liquid crystal materials (two-frequency driving liquid crystal materials; including liquid crystal materials of <0), cholesteric liquid crystal materials (specifically, liquid crystal materials having a selective reflection characteristic with respect to visible light), smectic liquid crystal materials, ferroelectric liquid crystal materials (SmC*), and discotic liquid crystal materials. These liquid crystal materials can be mixed together. Specifically, nematic liquid crystal materials or nematic liquid crystal materials mixed with cholesteric liquid crystal materials are preferable. Liquid crystal materials having a sufficient resistance against chemical reaction are more preferable since treatment of the liquid crystal materials accompanies the photopolymerization reaction.

[Orientation of Liquid Crystal Molecules]

In the liquid crystal domains, the liquid crystal molecules can be oriented in either one of a twisted nematic (TN) manner, super-twisted nematic (STN) manner, electrically controlled birefringence (ECB) manner, surface stabilized ferroelectric liquid crystal (SSFLC) manner, and the like. The liquid crystal molecules can also be oriented in an axially symmetrical manner, e.g., concentrically, helically, or radially.

(Production Method of Liquid Crystal Layer)

The inventors of the present invention have examined a method for arranging liquid crystal droplets having a size substantially identical to the size of one pixel so that one droplet is substantially allocated to one pixel. As a result, the following methods have been found effective.

1) The liquid crystal layer is irradiated with ultraviolet (UV) light which has regular illumination defective spots having a size similar to the diameter of the liquid crystal droplets which is substantially the same as the size of one pixel, and an area corresponding to a majority of one pixel is shaded from the UV light. In this way, an LCD device having liquid crystal domains surrounded by a polymer wall or a wall structure can be produced.

2) A material having different free energies at the interfaces with a liquid crystal phase and an isotropic phase is previously formed on a substrate and patterned. A liquid crystal phase is then provided on the patterned material, for example, so that the free energy of the material is patterned and controlled. In this way, an LCD device having liquid crystal domains surrounded by a polymer wall or a wall structure can be produced.

(Retardation d n)

In the LCD device according to the present invention provided with polarizers, the viewing angle characteristic is degraded when viewed in a 45 direction from the polarization axes of the polarizers. This is because (1) the polarizers have the viewing angle characteristic thereof and (2) the liquid crystal layer has a retardation d n.

The reason (2) above is described in more detail. Light incident on the liquid crystal layer along the polarization axis of a polarizer includes only a component of ordinary light or extraordinary light when it crosses an index ellipsoid of the liquid crystal layer. On the contrary, light incident on the liquid crystal layer in a 45 direction from the polarization axis of the polarizer includes both components of ordinary light and extraordinary light when it crosses an index ellipsoid of the liquid crystal layer. For such light, the polarizing axes of the two polarizers which are perpendicular to each other are apparently parallel to each other. The light therefore becomes elliptically polarized light, resulting in significant light leakage.

In order to solve the above problem, the retardation of the liquid crystal layer is preferably made as small as possible to suppress the generation of elliptically polarized light.

However, a light transmittance of the liquid crystal layer when no voltage is applied ($T_0$) is affected by the retardation thereof. Accordingly, in order to secure the omnidirectionality of the viewing angle characteristic and the brightness of the display, the retardation of the liquid crystal layer is preferably in the range from about 300 nm to about 650 nm. If the retardation is less than about 300 nm, the brightness is not secured at white display resulting in a dark display. If the retardation exceeds about 650 nm, gradation inversion occurs in the viewing angle characteristic, reducing the angle of visibility of the panel.

The twisting angle of the liquid crystal molecules is preferably in the range from about 45 to about 150 In particular, an angle in the vicinity of about 90 which satisfies a first minimum condition is preferable since it provides the brightest display.

(Driving Method)

An LCD device according to the present invention can be driven in various methods including simple matrix driving, plasma address driving, or active matrix driving using switching devices such as a-Si (amorphous silicon) TFTs (thin film transistors), p-Si (polycrystalline silicon) TFTs, or MIM (metal-insulator-metal) device.

(Substrate Material)

Substrates usable in the present invention include a glass substrate and a plastic substrate made of a polymerfilm, as transparent solid materials. Opaque solid materials such as a substrate coated with a metal thin film and an Si substrate can also be used.

A substrate coated with a metal thin film is effective for a reflection-type LCD device.

A plastic substrate is preferably made of a material which does not absorb visible light, such as PET, an acrylic polymer, styrene, and polycarbonate. Alternatively, the plastic substrate itself may be provided with the polarization ability.

A laminated substrate composed of two different types of plates may be used. A laminated substrate composed of two plates of the same type or different types having different thicknesses may also be used.

Hereinbelow, the present invention is described by way of illustrative, non-limiting examples with reference to the accompanying drawings. Note that the following codes used in the description of the examples refer to the terms as follows.

GC: gas chromatography
HPLC: high performance liquid chromatography
TLC: thin layer chromatography
IR::infrared absorption spectrum
Mass: mass spectrum
b.p.: boiling point
m.p: melting point
Y: yield

SYNTHESIS EXAMPLE 1

Synthesis of Polymerizable compound 4-(trans-4-pentylcyclohexyl)-4'-vinylbiphenyl represented by Formula (A)

formula (A)

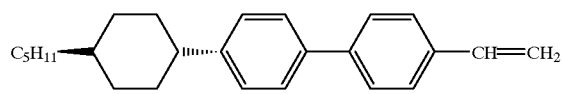

(1-a) Synthesis of compound 4-acetyl-4'-(trans-4-pentylcyclohexyl)biphenyl represented by formula:

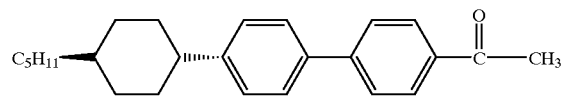

First, 23.6 g of anhydrous aluminum chloride and 120 ml of methylene chloride were put in a 300 ml flask. After 14.0 g of acetyl chloride was dropped into the mixture at 5° C. or less, the resultant mixture was stirred keeping the same temperature for 30 minutes. Then, 45.2 g of 4-(trans-4-pentylcyclohexyl)biphenyl was added to resultant mixture at 5° C. or less and stirred for 30 minutes at room temperature. After the reaction, the reaction solution was poured into dilute hydrochloric acid, and an organic layer was separated. The organic layer was then washed with water and dried with sodium sulfate. The solvent was then distilled off. The residue was recrystallized from acetone to obtain 24.0 g (Y: 46.0%) of 4-acetyl-4'-(trans-4-pentylcyclohexyl)biphenyl. The purity of the resultant compound was 99.7% as measured by GC.

(1-b) Synthesis of compound 4-(1-hydroxyethyl)-4'-(trans-4-pentylcyclohexyl)biphenyl represented by formula:

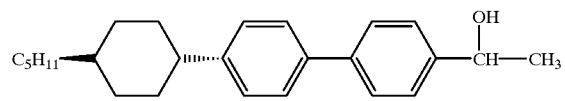

First, 1.09 g of lithium aluminum hydride and 50 ml of tetrahydrofuran dehydrated were put in an argon-replaced 200 ml flask. Then, 50 ml of tetrahydrofuran dehydrated containing 10. 0 g of the 4-acetyl-4'-(trans-4-pentylcyclohexyl)biphenyl obtained from the synthesis (1-a) above dissolved therein was dropped into the resultant mixture while being stirred. After the dropping, the resultant mixture was stirred under reflux for two hours. After the reaction, ethyl acetate and subsequently 2N hydrochloric acid were added to acidify the reaction solution and thus to deactivate non-reacted lithium aluminum hydride. Ether was added to the reaction solution to separate an ether layer. The ether layer was washed with water and dried with sodium sulfate. The solvent was then distilled of f. The residue was recrystallized from acetone to obtain 9.42 g (Y: 97.3%) of 4-(1-hydroxyethyl)-4'-(trans-4-pentylcyclohexyl)biphenyl. The purity of the resultant compound was 99.8% as measured by HPLC.

(1-c) Synthesis of 4-(trans-4-pentylcyclohexyl)-4'-vinylbiphenyl represented by formula (A) above First, 9.39 g of 4-(1-hydroxyethyl)-4'-(trans-4-pentylcyclohexyl)biphenyl, 0.52 g of potassium hydrogensulfate, and 50 ml of toluene were put in a 300 ml flask provided with a water content quantitative tube, and subjected to azeotropic dehydration under reflux for four hours. After the reaction, ether was added to the reaction solution, which was then washed with a saturated brine, and dried with sodium sulfate. The solvent was then distilled off. The residue was recrystallized from hexane to obtain 1.88 g (Y: 21.1%) of 4-(trans-4-pentylcyclohexyl)vinylbiphenyl. The purity of the resultant compound was 100.0% as measured by GC, 99.9% as measured by HPLC, and 1 spot as measured by TLC. The phase transfer temperature of the resultant compound was as follows.

crystal —74.2° C.→ smectic X phase —140° C.→ polymerization

It was confirmed from the IR measurement result and Mass analysis that a molecular ion peak was recognized at 332 and that the resultant substance was the compound represented by formula (A) above in consideration of the materials used.

SYNTHESIS EXAMPLE 2

Synthesis of Polymerizable Compound 4-(trans-4-pentylcyclohexyl)-4-(1-methylvinyl)biphenyl Represented by Formula (B)

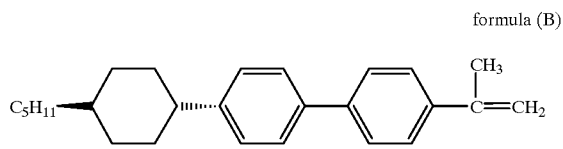

formula (B)

First, 0.38 g of magnesium and 1 ml of dehydrated ether were put in an argon-replaced 50 ml flask, and 0.2 g of methyl iodide was added to activate the magnesium. Then, 10 ml of dehydrated ether containing 1.92 g of methyl iodide dissolved therein was dropped into the mixture while being stirred. After the dropping, the resultant mixture was stirred at room temperature for one hour. Thereafter, 40 ml of anhydrous tetrahydrofuran containing 4.18 g of 4-acetyl-4'-(trans-4-pentylcyclohexyl)biphenyl obtained from the synthesis (1-a) above dissolved therein was dropped into the resultant mixture while being stirred, and stirred under reflux for one hour. After the reaction, 3N hydrochloric acid was added to acidify the reaction solution, and ether was added to form an ether layer, and the ether layer was separated. The ether layer was washed with a saturated brine and dried with sodium sulfate. The solvent was then distilled off.

Thereafter, the above residue, 0.25 g of potassium hydrogensulfate, 0.15 g of 4-methoxyphenol, and 100 ml of toluene were put in a 200 ml flask provided with a water content quantitative tube, and subjected to azeotropic dehydration under reflux for two hours. After the reaction, the reaction solution was washed with a saturated brine and dried with sodium sulfate. The solvent was then distilled off. The residue was purified by silica gel column chromatography (eluent:hexane) and recrystallized from acetone, to obtain 1.63 g (Y: 39.2%) of 4-(trans-4-pentylcyclohexyl)-4'-(1-methylvinyl)biphenyl. The purity of the resultant compound was 100.0% as measured by GC, 99.8% as measured by HPLC, and 1 spot as measured by TLC. The phase transfer temperature of the resultant compound was as follows.

crystal —89.2° C.→ smectic B phase —186.0° C.→
smectic A phase —192.2° C.→ nematic phase —196.8° C.→ isotropic phase It was confirmed from the IR measurement result and Mass analysis that a molecular ion peak was recognized at 346 and that the resultant substance was the compound represented by formula (B) above in consideration of the materials used.

SYNTHESIS EXAMPLE 3

Synthesis of Polymerizable compound 2,3-difluoro-4'-(trans-4-pentylcyclohexyl)-4-vinylbiphenyl Represented by Formula (C)

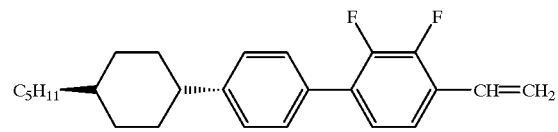

formula (C)

(3-a) Synthesis of compound 2,3-difluorophenylboronic acid represented by formula:

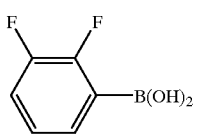

First, 100 g of 1,2-difluorobenzene and 350 ml of dehydrated tetrahydrofuran were put in an argon-replaced 2 flask, and cooled to −60° C. Then, 700 ml of a hexane solution containing n-butyllithium at a concentration of 1.6 mol/l was dropped into the resultant mixture while being stirred for two hours, and further stirred keeping the same temperature for another two hours. Subsequently, 175 g of trimethyl borate was dropped and stirred keeping the same temperature for one hour. The resultant mixture was left to gradually resume room temperature, stirred for eight hours, and again cooled to 0° C. The resultant reaction solution was poured into dilute hydrochloric acid to acidify the reaction solution. Toluene was then added, and the resultant toluene layer was washed with a saturated brine and dried with sodium sulfate. The solvent was then distilled off. The crystallized residue was immersed in a heated hexane solution and washed, to obtain 80.8 g of 2,3-difluorophenylboronic acid. The purity of the resultant compound was 99.5% as measured by HPLC.

(3-b) Synthesis of compound 2,3-difluoro-4'-(trans-4-pentylcyclohexyl)biphenyl represented by formula:

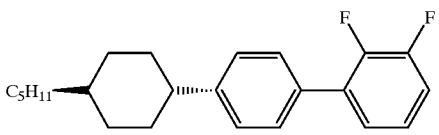

First, 500 ml of benzene containing 144.6 g of 1-bromo-4-(trans-4-pentylcyclohexyl)benzene dissolved therein, 400 ml of ethanol containing 78 g of 2,3-difluorophenyl boronic acid obtained from the synthesis (3-a) above, 500 ml of a sodium carbonate aqueous solution with a concentration of 2.0 mol/l, and 15 g of tetrakis(triphenylphosphine)palladium (0) were put in an argon-replaced 3 flask, and stirred under reflux for six hours. After the reaction, water and toluene were added to the reaction solution f or extraction. The resultant organic layer was washed with a saturated brine and dried with sodium sulfate. The solvent was then distilled off. The residue was purified by silica gel column chromatography (eluent:hexane) to obtain 109 g (Y: 69.9%) of 2,3-difluoro-4'-(trans-4-pentylcyclohexyl)biphenyl. The purity of the resultant compound was 98.0% as measured by HPLC.

(3-c) Synthesis of compound 2,3-difluoro-4-formyl-4'-(trans-4-pentylcyclohexyl)biphenyl represented by formula:

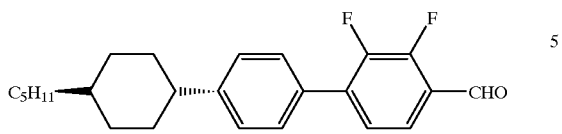

First, 24.2 g of 2,3-difluoro-4'-(trans-4-pentylcyclohexyl)biphenyl obtained from the synthesis (3-b) above and 100 ml of dehydrated tetrahydrofuran were put in an argon-replaced 300 ml flask. The resultant reaction solution was cooled to −60° C. Then, 60 ml of a hexane solution containing n-butyllithium at a concentration of 1.6 mol/l was dropped into the reaction solution while being stirred for two hours, and further stirred keeping the same temperature for three hours. Subsequently, 20 ml of dehydrated tetrahydrofuran containing 6.2 g of dimethylformaldehyde dissolved therein was dropped while being stirred keeping the same temperature. The resultant reaction solution was left to gradually resume room temperature, and stirred for eight hours. After the reaction, the resultant reaction solution was poured into dilute hydrochloric acid to acidify the reaction solution. Toluene was added to the resultant solution for extraction. The resultant toluene layer was washed with a saturated brine and dried with sodium sulfate. The solvent was then distilled off. The residue was recrystallized from hexane, to obtain 13.4 g (Y: 58.4%) of 2,3-difluoro-4-formyl-4'-(trans-4-pentylcyclohexyl)biphenyl. The purity of the resultant compound was 99.9% as measured by HPLC.

(3-d) Synthesis of 2,3-difluoro-4'-(trans-4-pentylcyclohexyl)-4-vinylbiphenyl represented by formula (C) above First, 3.71 g of t-butoxy potassium, 13.36 g of methyltriphenylphosphonium iodide, and 100 ml of dehydrated tetrahydrofuran were put in an argon-replaced 200 ml flask, and stirred while icing for 30 minutes. Then, 50 ml of dehydrated tetrahydrofuran containing 9.0 g of 2,3-difluoro-4-formyl-4'-(trans-4 -pentylcyclohexyl)biphenyl obtained from the synthesis (3-c) above dissolved therein was dropped to the resultant mixture while being stirred keeping the same temperature. After the dropping, water and ether were added for extraction, and the resultant ether layer was washed with a saturated brine and dried with sodium sulfate. The solvent was then distilled off. The residue was purified by silica gel column chromatography (eluent:hexane) and recrystallized from acetone, to obtain 0.67 g (Y: 7.5%) of 2,3-difluoro-4'-(trans-4-pentylcyclohexyl)-4-vinylbiphenyl. The purity of the resultant compound was 100.0% as measured by GC, 99.5% as measured by HPLC, and 1 spot as measured by TLC. The phase transfer temperature of the resultant compound was as follows.

crystal $\xrightarrow{36.0° C.}$ smectic A phase $\xrightarrow{92.1° C.}$ nematic phase $\xrightarrow{124.9° C.}$ polymerization It was confirmed from the IR measurement result and Mass analysis that a molecular ion peak was recognized at 368 and that the resultant substance was the compound represented by formula (C) above in consideration of the materials used.

SYNTHESIS EXAMPLE 4

Synthesis of polymerizable compound 2-fluoro-4'-(trans-4-pentylcyclohexyl)-4-vinylbiphenyl represented by formula (D)

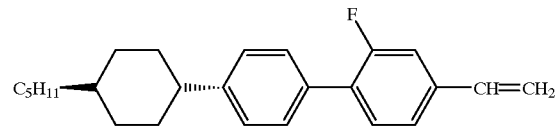

formula (D)

(4-a) Synthesis of compound 4-bromo-2-fluoro-4'-(trans-4-pentylcyclohexyl)biphenyl represented by formula:

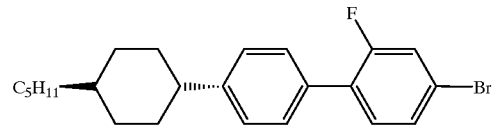

First, 150 ml of ethanol containing 17.84 g of 4-(trans-4-pentylcyclohexyl)phenylboronic acid dissolved therein, 150 ml of benzene containing 15.0 g of 4-bromo-2-fluoro-1-iodobenzene dissolved therein, 49.8 ml of a sodium carbonate aqueous solution with a concentration of 2.0 mol/l, and 1.44 g of tetrakis(triphenylphosphine)palladium(0) were put in an argon-replaced 500 ml flask, and stirred under reflux for 37 hours. After the reaction, water and ether were added to the reaction solution for extraction. The resultant ether layer was washed with a saturated brine and dried with sodium sulfate. The solvent was then distilled off. The residue was purified by silica gel column chromatography (eluent:hexane) and recrystallized from hexane, to obtain 13.6 g (Y: 67.8%) of 4-bromo-2-fluoro-4'-(trans-4-pentylcyclohexyl)biphenyl. The purity of the resultant compound was 99.5% as measured by GC.

(4-b) Synthesis of 2-fluoro-4'-(trans-4-pentylcyclohexyl)-4-vinylbiphenyl represented by formula (D) above First, 10.0 g of 4-bromo-2-fluoro-4'-(trans-4-pentylcyclohexyl)biphenyl obtained from the synthesis (4-a) above, 9.43 g of tributylvinyltin, 0.58 g of tetrakis(triphenylphosphine)palladium(0), 0.03 g of p-methoxyphenol, and 150 ml of anhydrous toluene were put in an argon-replaced 300 ml flask, and stirred under reflux for 18 hours. After the stirring, insoluble material was filtered off, and ether was added to the resultant filtrate to separate an organic layer. The organic layer was washed with 5% ammonia water, further washed with a saturated brine and dried with sodium sulfate. The solvent was then distilled off. The residue was purified by silica gel column chromatography (eluent:hexane) and recrystallized from hexane, to obtain 6.72 g (Y: 77.3%) of 2-fluoro-4'-(trans-4-pentylcyclohexyl)-4-vinylbiphenyl. The purity of the resultant compound was 100.0% as measured by GC, 99.9% as measured by HPLC, and 1 spot as measured by TLC. The phase transfer temperature of the resultant compound was as follows.

crystal $\xrightarrow{29.1° C.}$ smectic X phase $\xrightarrow{52.8° C.}$ nematic phase $\xrightarrow{137.2° C.}$ polymerization It was confirmed from the IR measurement result and Mass analysis that a molecular ion peak was recognized at 350 and that the resultant substance was the compound represented by formula (D) above in consideration of the materials used.

SYNTHESIS EXAMPLE 5

Synthesis of polymerizable compound 2,6-difluoro-4'-(trans-4-pentylcyclohexyl)-4-vinylbiphenyl represented by formula (E)

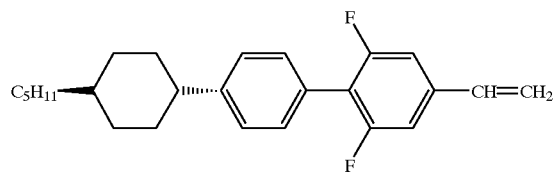

formula (E)

(5-a) Synthesis of compound 4-bromo-2,6-difluoro-4'-(trans-4-pentylcyclohexyl)biphenyl represented by formula:

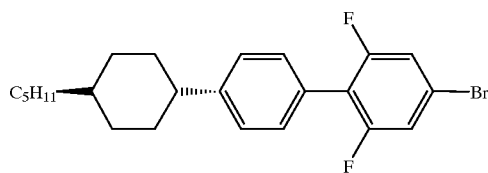

First, 50 ml of ethanol containing 5.61 g of 4-(trans-4-pentylcyclohexyl)phenylboronic acid dissolved therein, 50 ml of benzene containing 5.0 g of 4-bromo-2,6-difluoro-1-iodobenzene dissolved therein, 15.7 ml of a sodium carbonate aqueous solution with a concentration of 2.0 mol/l, and 0.45 g of tetrakis(triphenylphosphine)palladium(0) were put in an argon-replaced 200 ml flask, and stirred under reflux for 48 hours. After the reaction, water and ether were added to the reaction solution for extraction. The resultant ether layer was washed with a saturated brine and dried with sodium sulfate. The solvent was then distilled off. The residue was purified by silica gel column chromatography (eluent:hexane) and recrystallized from acetone, to obtain 2.58 g (Y: 39.1%) of 4-bromo-2,6-difluoro-4'-(trans-4-pentylcyclohexyl)biphenyl. The purity of the resultant compound was 100.0% as measured by GC. (5-b) Synthesis of polymerizable compound 2,6-difluoro-4'-(trans-4-pentylcyclohexyl)-4-vinylbiphenyl represented by formula (E) above First, 2.58 g of 4-bromo-2,6-difluoro-4'-(trans-4-pentylcyclohexyl)biphenyl obtained from the synthesis (5-a) above, 2.33 g of tributylvinyltin, 0.18 g of tetrakis(triphenylphosphine)palladium(0), 0.008 g of p-methoxyphenol, and 50 ml of anhydrous toluene were put in an argon-replaced 300 ml flask, and stirred under reflux for nine hours. After the reaction, insoluble material was filtered off, and 100 ml of water containing 50 ml of ether and 1.73 g of potassium fluoride dissolved therein was added to the filtrate and stirred. After the stirring, insoluble material was filtered off again, and an organic layer was separated.. The organic layer was washed with 5% ammonia water, further washed with a saturated brine, and dried with sodium sulfate. The solvent was then distilled off. The residue was purified by silica gel column chromatography (eluent:hexane) and recrystallized from hexane, to obtain 1.57 g (Y:.69.6%) of 2,6-difluoro-4'-(trans-4-pentylcyclohexyl)-4-vinylbiphenyl. The purity of the resultant compound was 100.0% as measured by GC, 99.7% as measured by HPLC, and 1 spot as measured by TLC. The phase transfer temperature of the resultant compound was as follows.

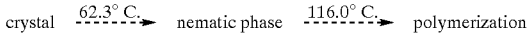

It was confirmed from the IR measurement result and Mass analysis that a molecular ion peak was recognized at 368 and that the resultant substance was the compound represented by formula (E) above in consideration of the materials used.

SYNTHESIS EXAMPLE 6

Synthesis of polymerizable compound 3-fluoro-4'-(trans-4-pentylcyclohexyl)-4-vinylbiphenyl represented by formula (F)

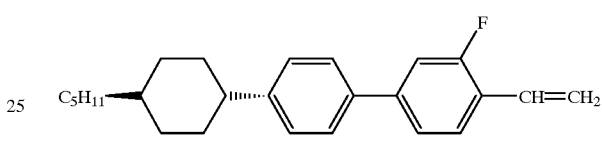

formula (F)

(6-a) Synthesis of compound 4-bromo-3-fluoro-4'-(trans-4-pentylcyclohexyl)biphenyl represented by formula:

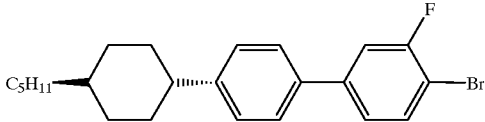

First, 100 ml of ethanol containing 11.89 g of 4-(trans-4-pentylcyclohexyl)phenylboronic acid dissolved therein, 100 ml of benzene containing 10.0 g of 1-bromo-2-fluoro-4-iodobenzene dissolved therein, 33.2 ml of a sodium carbonate aqueous solution with a concentration of 2.0 mol/l, and 0.96 g of tetrakis(triphenylphosphine)palladium(0) were put in an argon-replaced 500 ml flask, and stirred under reflux for 16 hours. After the reaction, water and ether were added to the reaction solution for extraction. The resultant ether layer was washed with a saturated brine and dried with sodium sulfate. The solvent was then distilled off. The residue was purified by silica gel column chromatography (eluent:hexane) and recrystallized from acetone, to obtain 11.6 g (Y: 86.8%) of 4-bromo-3-fluoro-4'-(trans-4-pentylcyclohexyl)biphenyl. The purity of the resultant compound was 100.0% as measured by GC.

(6-b) Synthesis of 3-fluoro-4'-(trans-4-pentylcyclohexyl)-4-vinylbiphenyl represented by formula (F) above First, 5.0 g of 4-bromo-3-fluoro-4'-(trans-4-pentylcyclohexyl)biphenyl obtained from the synthesis (6-a) above, 4.72 g of tributylvinyltin, 0.36 g of tetrakis(triphenylphosphine)palladium(0), 0.015 g of p-methoxyphenol, and 50 ml of anhydrous toluene were put in an argon-replaced 300 ml flask, and stirred under reflux for eight hours. After the reaction, insoluble material was filtered off, and 100 ml of water containing 10 ml of ethyl acetate and 1.73 g of potassium fluoride dissolved therein was added to the filtrate and stirred. After the stirring, insoluble material was filtered off again, and an organic layer was separated. The organic layer was washed with 5% ammonia water, further washed with a saturated brine, and dried with sodium sulfate. The solvent was then distilled off. The residue was purified by silica gel column chromatography (eluent: hexane) and recrystallized from hexane, to obtain 2.99 g (Y: 68.8%) of 3-fluoro-4'-(trans-4-pentylcyclohexyl)-4-vinylbiphenyl. The purity of the resultant compound was 100.0% as measured by GC, 99.3% as measured by HPLC, and 1 spot as measured by TLC. The phase transfer temperature of the resultant compound was as follows.

crystal $\xrightarrow{102.0° C.}$ smectic A phase $\xrightarrow{104.9° C.}$ nematic phase $\xrightarrow{108.9° C.}$ polymerization It was confirmed from the IR measurement result and Mass analysis that a molecular ion peak was recognized at 350 and that the resultant substance was the compound represented by formula (F) above in consideration of the materials used.

SYNTHESIS EXAMPLE 7

Synthesis of polymerizable compound 2.5-difluoro-4'-(trans-4-pentylcyclohexyl)-4-vinylbiphenyl represented by formula (G)

formula (G)

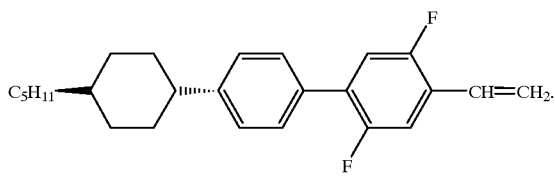

(7-a) Synthesis of compound 2,5-difluoro-4-nitro-4'-(trans-4-pentylcyclohexyl)biphenyl represented by formula:

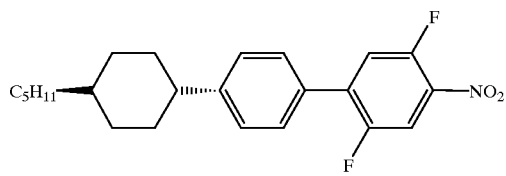

First, 50 ml of ethanol containing 7.52 g of 4-(trans-4-pentylcyclohexyl)phenylboronic acid dissolved therein, 50 ml of benzene containing 5.0 g of 4-bromo-2,5-difluoro-1-nitrobenzene dissolved therein, 21.0 ml of a sodium carbonate aqueous solution with a concentration of 2.0 mol/l, and 0.61 g of tetrakis(triphenylphosphine)palladium(0) were put in an argon-replaced 200 ml flask, and stirred under reflux for 12 hours. After the reaction, water and ether were added to the reaction solution for extraction. The resultant ether layer was washed with a saturated brine and dried with sodium :sulfate. The solvent was then distilled off. The residue was purified by silica gel column chromatography (eluent:toluene/hexane=1/4) and recrystallized from hexane, to obtain 6.87 g (Y: 84.4%) of 2,5-difluoro-4-nitro-4'-(trans-4-pentylcyclohexyl)biphenyl. The purity of the resultant compound was 100.0% as measured by GC. The phase transfer temperature of the compound was as follows.

crystal $\xrightarrow{58.4° C.}$ nematic phase $\xrightarrow{108.3° C.}$ isotropic phase (7-b) Synthesis of compound 4-amino-2,5-difluoro-4'-(trans-4-pentylcyclohexyl)biphenyl represented by formula:

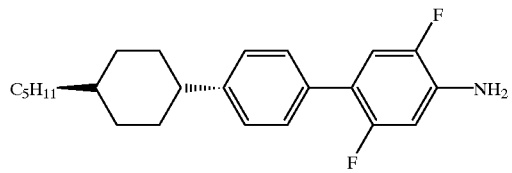

First, 6.86 g of 2,5-difluoro-4-nitro-4'-(trans-4-pentylcyclohexyl)biphenyl obtained from the synthesis (7-a) above, 1.25 g of 10% palladium carbon, and 100 ml of tetrahydrofuran were put in a 200 ml autoclave. The autoclave was then charged with hydrogen under a pressure of 10 kg/cm$^2$, and stirred at room temperature for six days. After the reaction, palladium carbon was filtered off, and the solvent was distilled off from the filtrate. The residue was purified by silica gel column chromatography (eluent:hexane/ethyl acetate 4/1) and recrystallized from hexane, to obtain 5.61 g (Y: 88.6%) of 4-amino-2,5-difluoro-4'-(trans-4-pentylcyclohexyl)biphenyl. The purity of the resultant compound was 100.0% as measured by GC, and m.p. was 68.3° C. to 70.4° C.

(7-c) Synthesis of compound 4-bromo-2,5-difluoro-4'-(trans-4-pentylcyclohexyl)biphenyl represented by formula:

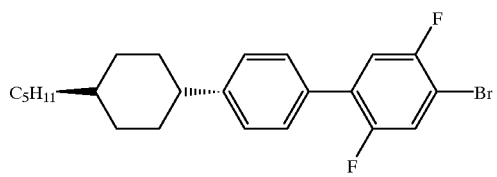

First, 8.1 ml of concentrated sulfuric acid, 1.1 g of sodium nitrite, and 20 ml of acetic acid were put in a 50 ml flask while icing. Then, 5.2 g of 4-amino-2,5-difluoro-4'-(trans-4-pentylcyclohexyl)biphenyl obtained from the synthesis (7-b) above was added as crystal to the resultant mixture, and stirred until the crystal was dissolved to be diazotized.

Then, 2.5 g of cuprous bromide, 6.6 ml of hydrobromic acid, and 20 ml of acetic acid were put in a 100 ml flask. The solution of the above diazo compound was dropped into the resultant mixture and stirred for 24 hours. After the reaction, ether and 21 ml of 50% sodium hydroxide were added to the reaction solution, and then sodium carbonate was added to neutralize the reaction solution, to separate an ether layer. The resultant ether layer was washed with a 1N potassium carbonate aqueous solution and dried with sodium sulfate. The solvent was then distilled off. The residue was purified by silica gel column chromatography (eluent:hexane) and recrystallized from acetone, to obtain 3.7 g (Y: 61.0%) of 4-bromo-2,5-difluoro-4'-(trans-4-pentylcyclohexyl) biphenyl. The purity of the resultant compound was 99.6% as measured by GC.

(7-d) Synthesis of 2,5-difluoro-4'-(trans-4-pentylcyclohexyl)-4-vinylbiphenyl represented by formula (G)

First, 3.74 g of 4-bromo-2,5-difluoro-4'-(trans-4-pentylcyclohexyl)biphenyl obtained from the synthesis (7-c) above, 3.52 g of tributylvinyltin, 0.26 g of tetrakis (triphenylphosphine)palladium(0), 0.011 g of p-methoxyphenol, and 100 ml of dehydrated toluene were put in an argon-replaced 100 ml flask. The resultant mixture was heated to 105° C. and stirred for eight hours. After the reaction, insoluble material was filtered off again, and 200 ml of water containing 3.4 g of potassium fluoride was added to the filtrate and stirred for six hours. After the stirring, insoluble material was filtered off, and ether was added to the filtrate to separate an organic layer. The resultant organic layer was washed with 5% ammonia water, further washed again with a saturated brine, and dried with sodium sulfate. The solvent was then distilled off. The residue was purified by silica gel column chromatography (eluent:hexane) and recrystallized from acetone, to obtain 2.7 g (Y: 82.5%) of 2,5-difluoro-4'-(trans-4-pentylcyclohexyl)-4-vinylbiphenyl. The purity of the resultant compound was 99.5% as measured by GC, 99.5% as measured by HPLC, and 1 spot as measured by TLC. The phase transfer temperature of the resultant compound was as follows.

crystal $\xrightarrow{45.3° C.}$ nematic phase $\xrightarrow{123.1° C.}$ polymerization It was confirmed from the IR measurement result and Mass analysis that a molecular ion peak was recognized at 368 and that the resultant substance was the compound represented by formula (G) above in consideration of the materials used.

SYNTHESIS EXAMPLE 8

Synthesis of polymerizable compound 2,3-difluoro-1-[trans-4-(trans-4-propylcyclohexyl)cyclohexyl]-4-vinylbenzene represented by formula (H)

formula (H)

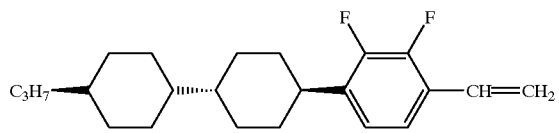

(8-a) Synthesis of compound 1,2-difluoro-3-[4-(trans-4-propylcyclohexyl)cyclohexenyl]benzene represented by formula:

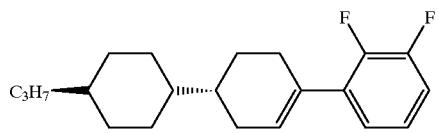

First, 46 g of 1,2-difluorobenzene and 240 ml of dehydrated tetrahydrofuran were put in an argon-replaced 2 flask, and cooled to −60° C. Then 315 ml of a hexane solution containing n-butyllithium at a concentration of 1.6 mol/l was dropped into the resultant mixture while being stirred for one hour, and further stirred keeping the same temperature for two hours. Subsequently, 470 ml of dehydrated tetrahydrofuran containing 80 g of 4-(trans-4-propylcyclohexyl)cyclohexane dissolved therein was dropped and stirred keeping the same temperature for two hours. The resultant mixtures was left to gradually resume room temperature, stirred for eight hours and cooled again to 0° C. The reaction solution was poured into dilute hydrochloric acid to acidify the reaction solution. Toluene was added to the resultant solution for extraction. The resultant toluene layer was washed with a saturated brine and dried with sodium sulfate. The solvent was then distilled off. The residue, 2 g of p-toluenesulfonic acid, and 1 of toluene were put in a 2 flask provided with a water content quantitative tube, and subjected to azeotropic dehydration under reflux for five hours. After the reaction, the reaction solution was washed with a saturated brine and dried with sodium sulfate. The solvent was then distilled off. The residue was distilled (b.p. 151° C./16 Pa) and recrystallized from acetone to obtain 55.7 g (Y: 48.6%) of 1,2-difluoro-3-[4-(trans-4-propylcyclohexyl)cyclohexenyl]benzene. The purity of the resultant compound was 98.0% as measured by GC.

(8-b) Synthesis of compound 1,2-difluoro-3-[4-(trans-4-propylcyclohexyl)cyclohexyl]benzene represented by formula:

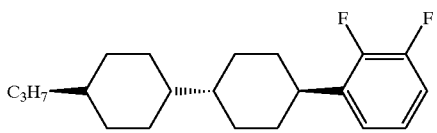

First, 55.7 g of 1,2-difluoro-3-[4-(trans-4-propylcyclohexyl)cyclohexenyl benzene obtained from the synthesis (8-a) above, 4.3 g of 10% palladium carbon, and 550 ml of ethyl acetate were put in a 1 autoclave. After the autoclave was charged with hydrogen so that a pressure of 3 kg/cm$^2$ was kept, the mixture was stirred at room temperature for three hours. After the reaction, palladium carbon was filtered off, and the solvent was distilled off from the filtrate. The residue, 30 g of potassium t-butoxide, and 200 ml of dehydrated dimethyl sulfoxide were put in an argon-replaced 500 ml flask, and stirred at 35° C. for three hours. After the reaction, the reaction solution was poured into dilute hydrochloric acid to acidify the reaction solution. Toluene was added to the resultant solution for extraction. The resultant toluene layer was washed with a saturated saline solution, and dried with sodium sulfate. The solvent was then distilled off. The residue was recrystallized from acetone, to obtain 40.0 g (Y: 71.4%) of 1,2-difluoro-3-[4-(trans-4-propylcyclohexyl)cyclohexyl]benzene. The purity of the resultant compound was 99.0% as measured by GC.

(8-c) Synthesis of compound 1-acetyl-2,3-difluoro-4-[trans-4-(trans-4-propylcyclohexyl)cyclohexyl]benzene represented by formula:

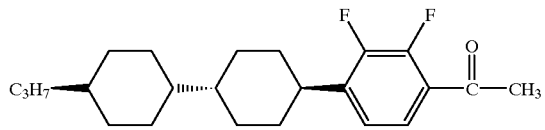

First, 5.9 g of anhydrous aluminum chloride and 30 ml of methylene chloride were put in a 100.ml flask. Then, 3.5 g of acetyl chloride was dropped into the mixture at 5° C. or less, and stirred keeping the same temperature for 30 minutes. Thereafter, 11.8 g of 1,2-difluoro-3-[4-(trans-4-propylcyclohexyl)cyclohexyl]benzene obtained from the synthesis (8-b) above was added to the resultant mixture at 5° C. or less, and stirred at room temperature for 30 minutes. After the reaction, the reaction solution was poured into dilute hydrochloric acid to separate an organic layer. The resultant organic layer was washed with water and dried with sodium sulfate. The solvent was then distilled off. The residue was recrystallized from acetone, to obtain 5.6 g (Y: 42.1%) of 1-acetyl-2,3-difluoro-4-[trans-4-(trans-4-propylcyclohexyl)cyclohexyl]benzene. The purity of the resultant compound was 99.4% as measured by GC.

(8-d) Synthesis of compound 1-(1-hydroxyethyl)-2,3-difluoro-4-[trans-4-(trans-4-propylcyclohexyl)cyclohexyl] benzene represented by formula:

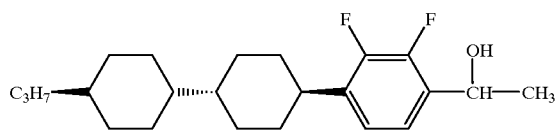

First, 0.1 g of lithium aluminum hydride and 20 ml of dehydrated tetrahydrofuran were put in an argon-replaced 200 ml flask. Then, 40 ml of dehydrated tetrahydrofuran containing 1.78 g of 1-acetyl-2,3-difluoro-4-[trans-4-(trans-4-propylcyclohexyl)cyclohexyl]benzene obtained from the synthesis (8-c) above dissolved therein was dropped into the resultant mixture while being stirred, and then stirred under reflux for six hours. After the reaction, 3N hydrochloric acid was added to the reaction solution to acidify the reaction solution, and thus to deactivate non-reacted lithium aluminum hydride. Ether was added to the reaction solution to separate an ether layer. The ether layer was washed with a saturated brine and dried with sodium sulfate. The solvent was then distilled off. The residue was purified by silica gel column chromatography (eluent:hexane/ethyl acetate=4/1), to obtain 1.41 g (Y: 78.8%) of 1-(1-hydroxyethyl)-2,3-difluoro-4-(trans-4-(trans-4-propylcyclohexyl)cyclohexyl] benzene. The purity of the resultant compound was 99.5% as measured by GC.

(8-e) Synthesis of polymerizable compound 2,3-difluoro-1-[trans-4-(trans-4-propylcyclohexyl)cyclohexenyl]-4-vinylbenzene represented by formula (H) above First, 1.49 g of 1-(1-hydroxyethyl)-2,3-difluoro-4-[trans-4-(trans-4-propylcyclohexyl)cyclohexyl]benzene obtained from the synthesis (8-d) above, 0.08 g of potassium hydrogensulfate, 0.05 g of p-methoxyphenol, and 50 ml of benzene were put in a 200 ml flask provided with a water content quantitative tube, and subjected to azeotropic dehydration under reflux for 16 hours. After the reaction, the reaction solution was washed with water and dried with sodium sulfate. The solvent was then distilled off. The residue was purified by silica gel column chromatography (eluent:hexane) and recrystallized from hexane, to obtain 0.70 g (Y: 21.1%) of 2,3-difluoro-1-[trans-4-(trans-4-propylcyclohexyl)cyclohexenyl]-4-vinylbenzene. The purity of the resultant compound was 100.0% as measured by GC, 99.9% as measured by HPLC, and 1 spot as measured by TLC. The phase transfer temperature of the resultant compound was as follows.

crystal $\xrightarrow{42.9°\text{C}}$ nematic phase $\xrightarrow{160°\text{C}}$ polymerization It was confirmed from the IR measurement result and Mass analysis that a molecular ion peak was recognized at 346 and that the resultant substance was the compound represented by formula (H) above in consideration of the materials used.

SYNTHESIS EXAMPLE 9

Synthesis of polymerizable compound 3-methyl-4'-(trans-4-pentylcyclohexyl)-4-vinylbiphenyl represented by formula (I)

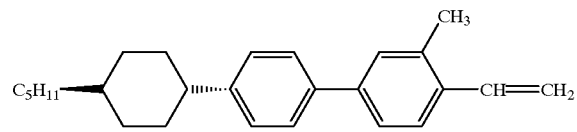

formula (I)

(9-a) Synthesis of compound 4-bromo-2-methylphenol represented by formula:

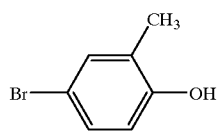

First, 70 ml of water, 25 ml of concentrated sulfuric acid, and 25.0 g of 4-bromo-2-methylaniline were put in a 500 ml flask. After 60 g of ice was added, 30 ml of water containing 10.9 g of sodium nitrite dissolved therein was dropped in 25 minutes keeping the temperature at 5° C. or less. Another 100 ml of water, 100 g of ice, and 1 g of urea were added and the resultant mixture was left for 30 minutes. Then, 50 g of anhydrous sodium sulfate, 70 ml of concentrated sulfuric acid, and 33 ml of water were put in a 500 ml flask provided with a distiller, and heated to a temperature of 130° C. to 135° C. The former reaction solution was dropped into the resultant mixture, and phenol generating was distilled together with steam. Ether was added to the distilled solution for extraction. The resultant ether layer was washed with water and a sodium hydrogencarbonate aqueous solution. A 10% sodium hydroxide aqueous solution was further added for extraction. Then, 35 ml of concentrated hydrochloric acid was added to the resultant sodium hydroxide aqueous solution to acidify the solution, and ether was added for extraction. The resultant ether layer was washed with water and dried with anhydrous sodium sulfate. The solvent was then distilled off under decompression. The residue was distilled (b.p.: 135° C. to 139° C./8 mmHg) to obtain 17.48 g (Y: 69.7%) of 4-bromo-2-methylphenol. The purity of the resultant compound was 98.8% as measured by GC.

(9-b) Synthesis of compound 4-bromo-2-methylphenyl methoxymethyl ether represented by formula:

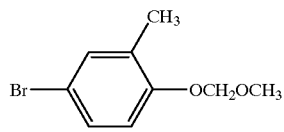

First, 80 ml of dehydrated methanol was put in a 300 ml flask provided with a calcium chloride tube. Then, 2.15 g of metal sodium was added, 25 ml of dehydrated methanol containing 17.48 g of 4-bromo-2-methylphenol obtained from the synthesis (9-a) above was dropped into the mixture, and the mixture was stirred for 30 minutes. The solvent was then distilled off under decompression. Toluene, 130 ml, was added to the residue, and the solvent was distilled off again under decompression. Under replacement with argon, 75 ml of dehydrated tetrahydrofuran was added to the residue, and 8.28 g of chloromethyl methyl ether was dropped while icing for 15 minutes. The resultant mixture was stirred keeping the same temperature for 30 minutes, and further stirred at room temperature for 30 minutes. A 2% sodium hydroxide aqueous solution, 200 ml, was added to the resultant reaction solution, and ether was added for extraction. The resultant ether layer was washed with water and a saturated brine, and dried with anhydrous sodium sulfate. The solvent was then distilled off. The residue was distilled (b.p. 142° C. to 150° C./8 mmHg) to obtain 18.03 g (Y: 83.4%) of 4-bromo-2-methylphenol methoxymethyl ether. The purity of the resultant compound was 92.7% as measured by GC.

(9-c) Synthesis of compound 4'-(trans-4-pentylcyclohexyl)-3-methylbiphenyl-4-yl methoxymethyl ether represented by formula:

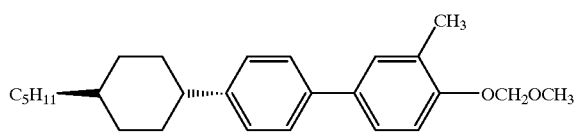

First, 125 ml of ethanol containing 21.1 g of 4-(trans-4-pentylcyclohexyl)phenylboronic acid dissolved-therein, 125 ml of benzene containing 16.2 g of 4-bromo-2-methylphenyl methoxymethyl ether obtained from the synthesis (9-c) above dissolved therein, 77.0 ml of a sodium carbonate aqueous solution at a concentration of 2 mol/l, and 2.02 g of tetrakis(triphenylphosphine)palladium(0) were put in an argon-replaced 500 ml flask, and stirred under reflux for five hours. After the reaction, water and toluene were added to the reaction solution for extraction. The resultant toluene layer was washed with a saturated brine and dried with sodium sulfate. The solvent was then distilled off. The residue was purified by silica gel column chromatography (eluent:toluene/hexane=1/1),to obtain 21.36 g (Y: 80.2%) of 4'-(trans-4-pentylcyclohexyl)-3-methylbiphenyl-4-yl methoxymethyl ether. The purity of the resultant compound was 97.2% as measured by GC.

(9-d) Synthesis of compound 4-[4-(trans-4-pentylcyclohexyl)phenyl]-2-methylphenol represented by formula:

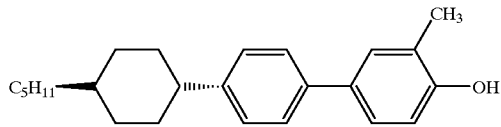

First, 21.36 g of 4'-(trans-4-pentylcyclohexyl)-3-methylbiphenyl-4-yl methoxymethyl ether obtained from the synthesis (9-d) above, 50 ml of 6N hydrochloric acid, 100 ml of tetrahydrofuran, and 10 ml of isopropyl alcohol were put in a 300 ml flask, and stirred under reflux for two hours. After the reaction, water and toluene were added to the reaction solution for extraction. The resultant toluene layer was washed with a saturated brine and dried with sodium sulfate. The solvent was then distilled off. The residue was recrystallized from methanol, to obtain 15.34 g (Y: 81.3%) of 4-[4-trans-4-pentylcyclohexyl)phenyl]-2-methylphenol. The purity of the resultant compound was 99.8% as measured by GC.

(9-e) Synthesis of compound 4-[4-(trans-4-pentylcyclohexyl)phenyl]-2-methylphenyl trifluoromethanesulfonate represented by formula:

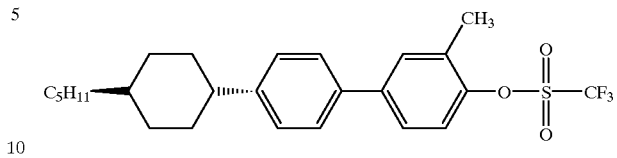

First, 10.1 g of 4-[4-trans-4-pentylcyclohexyl)phenyl]-2-methylphenol obtained from the synthesis (9-c) above and 50 ml of pyridine were put in a 200 ml flask provided with a calcium chloride tube, and a mixture was cooled to −20° C. Then, 9.31 g of trifluoromethanesulfonic anhydride was dropped into the mixture while being stirred. After the dropping, the resultant mixture was stirred at 0° C. for 24 hours. The reaction solution was poured to water, and ether was then added for extraction. The resultant ether layer was washed with 5% hydrochloric acid, further washed with a saturated brine, and dried with sodium sulfate. The solvent was then distilled off. The residue was purified by silica gel column chromatography (eluent:hexane), to obtain 13.38 g (Y: 95.2%) of 4-[4-(trans-4-pentylcyclohexyl)phenyl]-2-methylphenyl trifluoromethanesulfonate. The purity of the resultant compound was 85.8% as measured by GC.

(9-f) Synthesis of polymerizable compound 3-methyl-4'-(trans-4-pentylcyclohexyl)-4-vinylbiphenyl represented by formula (I) above First, 9.87 g of 4-[4-(trans-4-pentylcyclohexyl)phenyl]-2-methylphenyl trifluoromethanesulfonate obtained from the synthesis (9-e) above, 8.01 g of tributylvinyltin, 0.21 g of tris(dibenzylideneacetone)(chloroform)dipalladium(0), 0.19 g of tri(2-furyl)phosphine, 2.36 g of lithium chloride, several pieces of crystal of 2,6-di-tert-butyl-p-cresol, and 37 ml of dehydrated N-methylpirrolidone were put in an argon-replaced 100 ml flask, and stirred at 50° C. for eight hours. After the reaction, a saturated potassium fluoride aqueous solution and hexane were added to the reaction solution and stirred for one hour. Insoluble material was then filtered off, and an organic layer was separated from the filtrate. The organic layer was then washed with 5% ammonia water, further washed with a saturated brine, and dried with sodium sulfate. The solvent was then distilled off. The residue was purified by silica gel column chromatography (eluent:hexane) and recrystallized from hexane, to obtain 5.20 g (Y: 71.1%) of 3-methyl-4'-(trans-4-pentylcyclohexyl)-4-vinylbiphenyl. The purity of the resultant compound was 99.8% as measured by GC, 100.0% as measured by HPLC, and 1 spot as measured by TLC. The phase transfer temperature of the resultant compound was as follows.

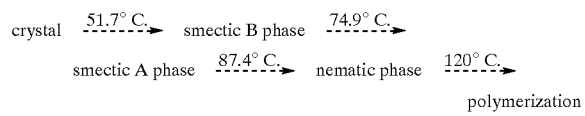

It was confirmed from the IR measurement result and Mass analysis that a molecular ion peak was recognized at 346 and that the resultant substance was the compound represented by formula (I) above in consideration of the materials used.

SYNTHESIS EXAMPLE 10

Synthesis of polymerizable compound 4-cyclohexyl-4-vinylbiphenyl represented by formula (J)

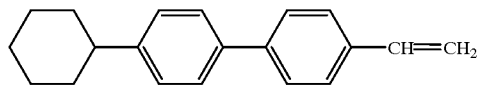

formula (J)

(10-a) Synthesis of compound 4-bromo-1-benzyloxybenzene represented by formula:

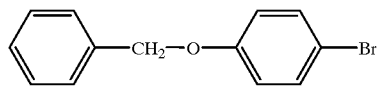

First, 53.2 g of benzyl chloride, 69.2 g of 4-bromophenol, 110.4 g of potassium carbonate, and 800 ml of methyl ethyl ketone were put in a 2 flask, and stirred under reflux for 30 minutes. After the reaction, insoluble material was filtered off, and the solvent was distilled off from the filtrate. Ether and a 2% sodium hydroxide aqueous solution were added to the residue to separate an organic layer. The organic layer was washed with a saturated brine and dried with sodium sulfate. The solvent was then distilled off. The residue was distilled (b.p. 131° C. to 140° C./0.08 mmHg), to obtain 61.0 g (Y: 58.07%) of 4-bromo-1-benzyloxybenzene. The purity of the resultant compound was 99.0% as measured by GC.

(10-b) Synthesis of compound 4-benzyloxyphenylboronic acid represented by formula:

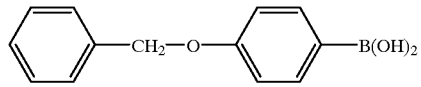

First, 5.07 g of magnesium and 80 ml of dehydrated tetrahydrofuran were put in an argon-replaced 500 ml flask. Some pieces of iodine were added to the mixture to activate the magnesium. Then, 100 ml of dehydrated tetrahydrofuran containing 45.7 g of 4-bromo-1-benzyloxybenzene obtained from the synthesis (10-a) above was dropped to the resultant mixture while being stirred. After the dropping, the reaction solution was stirred under reflux for 30 minutes, and cooled to −40° C. Then, 60 ml of dehydrated tetrahydrofuran containing 21.66 g of trimetyl borate was dropped to the reaction solution while being stirred. After being left to gradually resume room temperature, the reaction solution was stirred under reflux for 30 minutes. The reaction solution was then cooled to 0° C. again, and after the addition of 200 ml of 10% sulfuric acid, stirred for one hour. Toluene was added to the resultant solution to separate an organic layer. The organic layer was washed with a saturated brine and dried with sodium sulfate. The solvent was then distilled off. The residue was recrystallized from toluene, to obtain 36.5 g (Y: 92.1%) of 4-benzyloxyphenylboronic acid.

(10-c) Synthesis of compound 4-benzyloxy-4'-cyclohexylbiphenyl represented by formula:

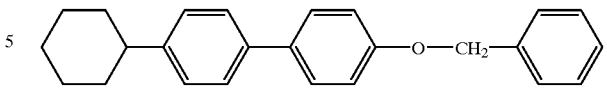

First, 80 ml of ethanol containing 7.18 g of 4-benzyloxyphenylboronic acid obtained from the synthesis (10-b) above dissolved therein, 50 ml of benzene containing 5.00 g of 1-bromo-4-cyclohexylbenzene dissolved therein, 21.0 ml of a sodium carbonate aqueous solution with a concentration of 2 mol/l, and 0.24 g of tetrakis(triphenylphosphine)palladium(0) were put in an argon-replaced 200 ml flask, and stirred under reflux for eight hours. After the reaction, water and toluene were added to the reaction solution for extraction. The resultant toluene layer was washed with a saturated brine and dried with sodium sulfate. The solvent was then distilled off. The residue was purified by silica gel column chromatography (eluent:toluene/hexane=1/4), to obtain 5.04 g (Y: 70.1%) of 4-benzyloxy-4'-cyclohexylbiphenyl. The purity of the resultant compound was 98.3% as measured by GC.

(10-d) Synthesis of compound 4-cyclohexyl-4'-hydroxybiphenyl represented by formula:

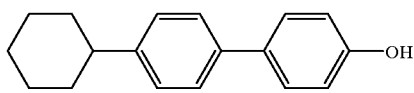

First, 5.04 g of 4-benzyloxy-4'-cyclohexylbiphenyl obtained from the synthesis (10-c) above, 0.52 g of 10% palladium carbon, and 100 ml of tetrahydrofuran were put in a 200 ml autoclave. After the autoclave was charged with hydrogen so that a pressure of 10 kg/cm$^2$ was kept, the mixture was stirred at room temperature for 48 hours. After the reaction, palladium carbon was filtered off, and the solvent was distilled off from the filtrate. The residue was recrystallized from a mixed solvent of acetone/hexane (1/3), to obtain 3.01 g (Y: 95.6%) of 4-cyclohexyl-4'-hydroxybiphenyl. The purity of the resultant compound was 100.0% as measured by GC.

(10-e) Synthesis of compound 4'-cyclohexylbiphenyl-4-yl trifluoromethanesulfonate represented by formula:

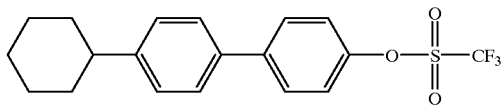

First, 2.95 g of 4-cyclohexyl-4'-hydroxybiphenyl obtained from the synthesis (10-d) above and 50 ml of pyridine were put in a 100 ml flask provided with a calcium chloride tube, and a mixture was cooled to −20° C. Then, 5.65 g of trifluoromethanesulfonic anhydride was dropped to the mixture while being stirred. After the dropping, the resultant mixture was stirred at 0° C. for 24 hours. The resultant reaction solution was poured to water, and ether was added for extraction. The resultant ether layer was washed with 5% hydrochloric acid, further washed with a saturated brine, and dried with sodium sulfate. The solvent was then distilled off. The residue was purified by silica gel column chromatography (eluent:hexane), to obtain 3.49 g (Y: 77.7%) of 4'-cyclohexylbiphenyl-4-yl trifluoromethanesulfonate. The purity of the resultant compound was 100.0% as measured by GC.

(10-f) Synthesis of polymerizable compound 4-cyclohexyl-4'-vinylbiphenyl represented by formula (J) above First, 3.49 g of 4'-cyclohexylbiphenyl-4-yl trifluoromethanesulfonate obtained from the synthesis (10-e) above, 3.45 g of tributylvinyltin, 0.09 g of tris(dibenzylideneacetone)(chloroform)dipalladium(0), 0.04 g of tri(2-furyl)phosphine, 1.15 g of lithium chloride, several pieces of crystal of 2,6-di-tert-butyl-p-cresol, and 30 ml of dehydrated N-methylpirrolidone were put in an argon-replaced 100 ml flask, and stirred at 50° C. for ten hours. After the reaction, a saturated potassium fluoride aqueous solution and hexane were added to the reaction solution and stirred for one hour. Insoluble material was then filtered off, and an organic layer was separated from the resultant filtrate. The organic layer was then washed with 5% ammonia water, further washed with a saturated brine, and dried with sodium sulfate. The solvent was then distilled off. The residue was purified by silica gel column chromatography (eluent:hexane) and recrystallized from hexane, to obtain 1.82 g (Y: 76.4%) of 4-cyclohexyl-4'-vinylbiphenyl. The purity of the resultant compound was 100.0% as measured by GC, 99.9% as measured by HPLC, and 1 spot as measured by TLC. The phase transfer temperature of the resultant compound was as follows.

crystal $\xrightarrow{114.6°\,C.}$ smectic B phase $\xrightarrow{121.4°\,C.}$ isotropic phase It was confirmed from the IR measurement result and Mass analysis that a molecular ion peak was recognized at 262 and that the resultant substance was the compound represented by formula (J) above in consideration of the materials used.

SYNTHESIS EXAMPLE 11

Synthesis of Polymerizable compound 2-trifluoromethyl-4'-(trans-4-pentylcyclohexyl)-4-vinylbiphenyl Represented by Formula (K)

formula (K)

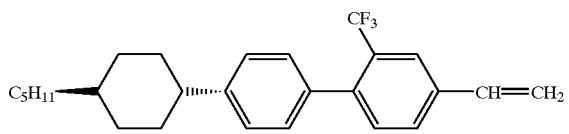

(11-a) Synthesis of compound 4'-(trans-4-pentylcyclohexyl)-2-trifluoromethyl-4-nitrobiphenyl represented by formula:

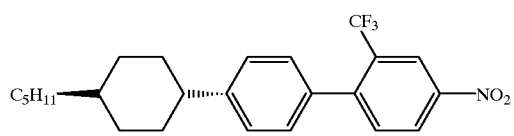

First, 100 ml of ethanol containing 6.57 g of 4-(trans-4-pentylcyclohexyl)phenylboronic acid dissolved therein, 100 ml of benzene containing 10.0 g of 2-trifluoromethyl-4-nitrobromobenzene dissolved therein, 37 ml of a sodium carbonate aqueous solution with a concentration of 2 mol/l, and 1.07 g of tetrakis(triphenylphosphine)palladium(0) were put in an argon-replaced 300 ml flask, and stirred under reflux for 12 hours. After the reaction, water and ether were added to the reaction solution for extraction. The resultant ether layer was washed with a saturated brine and dried with sodium sulfate. The solvent was then distilled off. The residue was purified by silica gel column chromatography (eluent:hexane/toluene=4/1), to obtain 14.2 g (Y: 91.3%) of 4'-(trans-4-pentylcyclohexyl)-2-trifluoromethyl-4-nitrobiphenyl. The purity of the resultant compound was 100.0% as measured by GC.

(11-b) Synthesis of compound 4-amino-2-trifluoromethyl-4'-(trans-4-pentylcyclohexyl)biphenyl represented by formula:

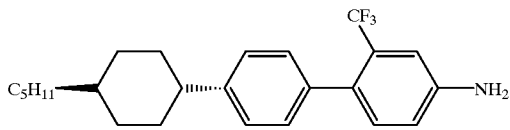

First, 14.19 g of 4'-(trans-4-pentylcyclohexyl)-2-trifluoromethyl-4-nitrobiphenyl obtained from the synthesis (11-a) above, 1.20 g of 10% palladium carbon, and 100 ml of tetrahydrofuran were put in a 500 ml autoclave. After the autoclave was charged with hydrogen so that a pressure of 10 kg/cm$^2$ was kept, the mixture was stirred at room temperature for three days. After the reaction, palladium carbon was filtered off, and the solvent was distilled off from the filtrate. The residue was purified by silica gel column chromatography (eluent:hexane/ethyl acetate=4/1), to obtain 12.8 g (Y: 87.5%) of 4-amino-2-trifluoromethyl-4'-(trans-4-pentylcyclohexyl)biphenyl. The purity of the resultant compound was 100.0% as measured by GC.

(11-c) Synthesis of compound 4-bromo-2-trifluoromethyl-4'-(trans-4-pentylcyclohexyl)biphenyl represented by formula:

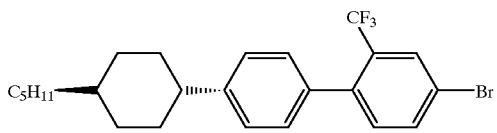

First, 18.3 ml of concentrated sulfuric acid was put in a 300 ml flask, and 2.5 g of sodium nitrite was added in a solid state while icing while being stirred. After the mixture was stirred for 30 minutes, 100 ml of acetic acid was added while icing. Then, 12.85 g of 4-amino-2-trifluoromethyl-4'-(trans-4-pentylcyclohexyl)biphenyl obtained from the synthesis (11-b) above was added to the resultant mixture in a solid state at room temperature, and stirred until it was dissolved, so as to diazotize the mixture. Then, 5.68 g of cuprous bromide, 18.7 ml of 48% hydrobromic acid, and 100 ml of acetic acid were put in a 500 ml flask of an eggplant shape. The solution of the above diazo compound was dropped into the resultant mixture and stirred at room temperature for 24 hours. After the reaction, diethyl ether and 303 ml of a 50% sodium hydroxide aqueous solution were added to the reaction solution, and then sodium carbonate was added until pH=7 was obtained. An ether layer was separated from the reaction solution. The ether layer was washed with a 1N potassium carbonate aqueous solution and dried with sodium sulfate. The solvent was then distilled off. The residue was purified by silica gel column chromatography (eluent:hexane), to obtain 11.81 g (Y: 74.7%) of 4-bromo-2-trifluoromethyl-4'-(trans-4-pentylcyclohexyl)biphenyl. The purity of the resultant compound was 100.0% as measured by GC, and m.p. was 51 to 52° C.

(11-d) Synthesis of polymerizable compound 2-trifluoromethyl-4'-(trans-4-pentylcyclohexyl)-4-vinylbiphenyl represented by formula (K) above First, 3.74 g of 4-bromo-2-trifluoromethyl-4'-(trans-4-pentylcyclohexyl)biphenyl obtained from the synthesis (11-c) above, 4.20 g of tributylvinyltin, 0.13 g of tetrakis (triphenylphosphine)palladium(0), 0.02 g of p-methoxyphenol, and 50 ml of dehydrated toluene were put in an argon-replaced 100 ml flask, heated to 115° C., and stirred for eight hours. After the reaction, insoluble material was filtered off, and 100 ml of water containing 1.7 g of potassium fluoride dissolved therein was added to the filtrate, and stirred for six hours. Insoluble material was filtered off again, and ether was added to the filtrate to separate an organic layer. The organic layer was washed with 5% ammonia water, further washed with a saturated brine, and dried with sodium sulfate. The solvent was then distilled off. The residue was purified by silica gel column chromatography (eluent:hexane) and recrystallized from acetone, to obtain 3.43 g (Y: 77.6%) of 2-trifluoromethyl-4'-(trans-4-pentylcyclohexyl)-4-vinylbiphenyl. The purity of the resultant compound was 100.0% as measured by GC, 99.8% as measured by HPLC, and 1 spot as measured by TLC. The phase transfer temperature of the compound was as follows.

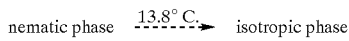

nematic phase  $\xrightarrow{13.8°\,C.}$  isotropic phase

It was confirmed from the IR measurement result and Mass analysis that a molecular ion peak was recognized at 400 and that the resultant substance was the compound represented by formula (K) above in consideration of the materials used.

SYNTHESIS EXAMPLE 12

Synthesis of Polymerizable Compound 3-trifluoromethyl-4'-(trans-4-pentylcyclohexyl)-4-vinylbiphenyl Represented by Formula (L)

formula (L)

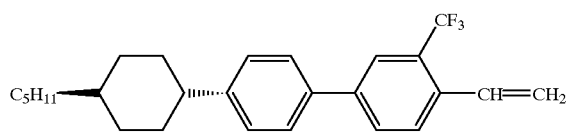

(12-a) Synthesis of compound 4-amino-4'-(trans-4-pentylcyclohexyl)-3-trifluoromethylbiphenyl represented by formula:

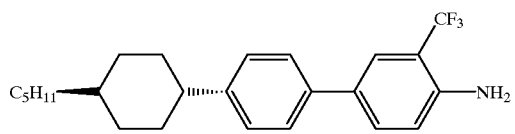

First, 100 ml of ethanol containing 4.91 g of 4-(trans-4-pentylcyclohexyl)phenylboronic acid dissolved therein, 100 ml of benzene containing 10.0 g of 2-trifluoromethyl-4-bromoaniline, 41.7 ml of a sodium carbonate aqueous solution with a concentration of 2 mol/l, and 1.20 g of tetrakis (triphenylphosphine)palladium(0) were put in an argon-replaced 300 ml flask, and stirred under reflux for six hours. After the reaction, water and ether were added to the reaction solution for extraction. The resultant ether layer was washed with a saturated brine and dried with sodium sulfate. The solvent was then distilled off. The residue was purified by silica gel column chromatography (eluent:hexane/toluene=4/1), to obtain 14.82 g (Y: 91.3%) of 4-amino-4'-(trans-4-pentylcyclohexyl)-3-trifluoromethylbiphenyl. The purity of the resultant compound was 99.2% as measured by GC.

(12-b) Synthesis of compound 4-bromo-3-trifluoromethyl-4'-(trans-4-pentylcyclohexyl)biphenyl represented by formula:

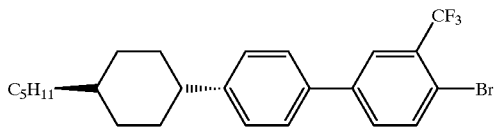

First, 21.1 ml of concentrated sulfuric acid was put in a 300 ml flask, and 2.89 g of sodium nitrite was added in a solid state while icing while being stirred. After the mixture was stirred for 30 minutes, 100 ml of acetic acid was added while icing. Then, 14.82 g of 4-amino-4'-(trans-4-pentylcyclohexyl)-3-trifluoromethylbiphenyl obtained from the synthesis (12-a) above was added to the resultant mixture in a solid state at room temperature, and stirred until it was dissolved, so as to diazotize the mixture. Then, 6.55 g of cuprous bromide, 21.5 ml of 48% hydrobromic acid, and 100 ml of acetic acid were put in a 500 ml flask of an eggplant shape. The solution of the above diazo compound was dropped into the resultant mixture and stirred at room temperature for 24 hours. After the reaction, diethyl ether and 417 ml of a 50% sodium hydroxide aqueous solution were added to the reaction solution, and then sodium carbonate was added until pH=7 was obtained. An ether layer was separated from the reaction solution. The ether layer was washed with a 1N potassium carbonate aqueous solution and dried with sodium sulfate. The solvent was then distilled off. The residue was purified by silica gel column chromatography (eluent:hexane), to obtain 4.94 g (Y: 28.6%) of 4-bromo-3-trifluoromethyl-4'-(trans-4-pentylcyclohexyl)biphenyl. The purity of the resultant compound was 99.1% as measured by GC.

(12-c) Synthesis of polymerizable compound 3-trifluoromethyl-4'-(trans-4-pentylcyclohexyl)-4-vinylbiphenyl represented by formula (L) above First, 4.94 g of 4-bromo-3-trifluoromethyl-4'-(trans-4-pentylcyclohexyl)biphenyl obtained from the synthesis (12-b) above, 4.14 g of tributylvinyltin, 0.13 g of tetrakis (triphenylphosphine)palladium(0), 0.0 g of p-methoxyphenol, and 50 ml of dehydrated toluene were put in an argon-replaced 100 ml flask, heated to 115° C., and stirred for eight hours. After the reaction, insoluble material was filtered off, and 100 ml of water containing 1.7 g of potassium fluoride dissolved therein was added to the filtrate, which was then stirred for six hours. Insoluble material was filtered off again, and ether was added to the filtrate to separate an organic layer. The organic layer was washed with 5% ammonia water, further washed with a saturated brine, and dried with sodium sulfate. The solvent was then distilled off. The residue was purified by silica gel column chromatography (eluent:hexane) and recrystallized from hexane, to obtain 3.03 g (Y: 69.4%) of 3-trifluoromethyl-4'-(trans-4-pentylcyclohexyl)-4-vinylbiphenyl. The purity of the resultant compound was 99.4% as measured by GC, 99.0% as measured by HPLC, and 1 spot as measured by TLC. The phase transfer temperature of the compound was as follows.

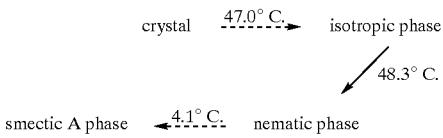

It was confirmed from the IR measurement result and Mass analysis that a molecular ion peak was recognized at 400 and that the resultant substance was the compound represented by formula (L) above in consideration of the materials used.

SYNTHESIS EXAMPLE 13

Synthesis of Polymerizable Compound 4'-perfluorobutyl-4-vinylbiphenyl Represented by Formula (M)

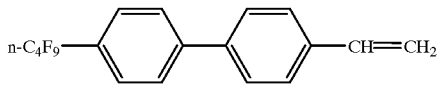

formula (M)

(13-a) Synthesis of compound 4-benzyloxy-4'-bromobiphenyl represented by formula:

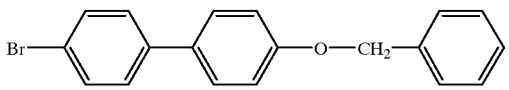

First, 25.0 g of benzyl bromide, 36.42 g of 4'-bromo-4-hydroxybiphenyl, 36.4 g of potassium carbonate, and 300 ml of methyl ethyl ketone were put in a1 flask, and stirred under reflux for six hours. After the reaction, 300 ml of tetrahydrofuran was added to the reaction solution, and a mixture was cooled to ambient temperature. Insoluble material was filtered off, and toluene was added to the filtrate to separate an organic layer. The organic layer was washed with a saturated brine and dried with sodium sulfate. The solvent was then distilled off. The residue was recrystallized from acetone, to obtain 42.56 g (Y: 85.8%) of 4-benzyloxy-4'-bromobiphenyl. The purity of the resultant compound was 99.0% as measured by GC.

(13-b) Synthesis of compound 4-benzyloxy-4'-perfluorobutylbiphenyl represented by formula:

First, 13.5 g of 4-benzyloxy-4'-bromobiphenyl obtained from the synthesis (13-a) above, 12.65 g of copper powder, and 40 ml of dehydrated dimethyl sulfoxide were put in an argon-replaced 200 ml flask, and heated to 60° C. Then, 15.15 g of perfluorobutyl iodide was dropped into the mixture. The resultant mixture was kept at the same temperature for two hours, was gradually raised to 110° C., and then stirred for four hours. The mixture was then cooled to 60° C. again, and 6.90 g of perfluorobutyl iodide and 6.83 g of copper powder were added to the mixture, which were gradually raised to 110° C. and then stirred for six hours. After the reaction, chloroform was added to the reaction solution and stirred. Insoluble material was filtered off, and the filtrate was washed with a saturated brine and dried with sodium sulfate. The solvent was then distilled off. The residue was purified by silica gel column chromatography (eluent:hexane/toluene=6/1) and recrystallized from acetone, to obtain 17.08 g (Y: 89.7%) of 4-benzyloxy-4'-perfluorobutylbiphenyl. The purity of the resultant compound was 96.2% as measured by GC, and m.p. was 128° C. to 134° C.

(13-c) Synthesis of compound 4'-perfluorobutyl-4-hydroxybiphenyl represented by formula:

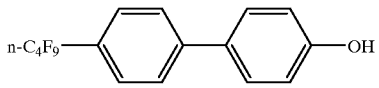

First, 16.6 g of 4-benzyloxy-4'-perfluorobutylbiphenyl obtained from the synthesis (13-b) above, 1.0 g of 10% palladium carbon, and 110 ml of tetrahydrofuran were put in a 500 ml autoclave. After the autoclave was charged with hydrogen so that a pressure of 3 kg/cm² was kept, the mixture was stirred at room temperature for 24 hours. After the reaction, palladium carbon was filtered off, and the solvent was distilled off from the filtrate. The residue was recrystallized from toluene, to obtain 9.35 g (Y: 69.4%) of 4'-perfluorobutyl-4-hydroxybiphenyl. The purity of the resultant compound was 98.3% as measured by GC, and m.p. was 131° C. to 134° C.

(13-d) Synthesis of compound 4'-perfluorobutylbiphenyl-4-yl trifluoromethanesulfonate represented by formula:

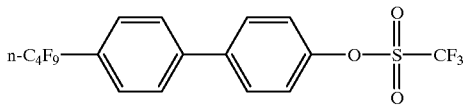

First, 1.24 g of 4'-perfluorobutyl-4-hydroxybiphenyl obtained from the synthesis (13-c) above and 50 ml of pyridine were put in a 100 ml flask provided with a calcium chloride tube, and cooled to −20° C. Then, 1.09 g of trifluoromethanesulfonic anhydride was dropped to the mixture while being stirred. After the dropping, the resultant mixture was stirred at 0° C. for 24 hours. The resultant reaction solution was poured into water, and ether was added for extraction. The resultant ether layer was washed with 5% hydrochloric acid, further washed with a saturated brine, and dried with sodium sulfate. The solvent was then distilled off. The residue was purified by silica gel column chromatography (eluent:hexane/toluene=9/1), to obtain 1.46 g (Y: 87.8%) of 4'-perfluorobutylbiphenyl-4-yl trifluoromethanesulfonate. The purity of the resultant compound was 99.8% as measured by GC.

(13-e) Synthesis of polymerizable compound 4'-perfluorobutyl-4-vinylbiphenyl represented by formula (M) above First, 1.46 g of 4'-perfluorobutylbiphenyl-4-yl trifluoromethanesulfonate obtained from the synthesis (13-d) above, 1.10 g of tributylvinyltin, 0.02 g of tris (dibenzylideneacetone)(chloroform)dipalladium(0), 0.02 g of tri(2-furyl)phosphine, 0.06 g of 2,6-di-tert-butyl-p-cresol, 0.36 g of lithium chloride, and 20 ml of dehydrated N-methylpirrolidone were put in an argon-replaced 100 ml flask, and stirred at 50° C. for eight hours. After the reaction, a saturated potassium fluoride aqueous solution and ether were added to the reaction solution and stirred for one hour.

Insoluble material was then filtered off, and an organic layer was separated from the resultant filtrate. The organic layer was then washed with 5% ammonia water, further washed with a saturated brine, and dried with sodium sulfate. The solvent was then distilled off. The residue was purified by silica gel column chromatography (eluent:hexane) and recrystallized from hexane, to obtain 0.74 g (Y: 66.2%) of 4'-perfluorobutyl-4-vinylbiphenyl. The purity of the resultant compound was 99.9% as measured by HPLC, and 1 spot as measured by TLC. The phase transfer temperature of the resultant compound was as follows.

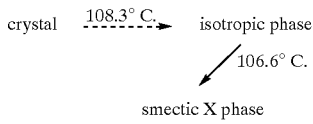

It was confirmed from the IR measurement result and Mass analysis that a molecular ion peak was recognized at 398 and that the resultant substance was the compound represented by formula (M) above in consideration of the materials used.

SYNTHESIS EXAMPLE 14

Synthesis of Polymerizable Compound 4'-[2-(perfluorobutyl)ethyloxy]-4-vinylbiphenyl Represented by Formula (N)

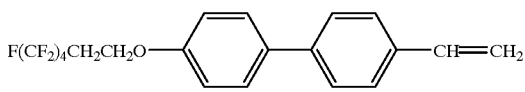

formula (N)

(14-a) Synthesis of compound 2-(perfluorobutyl)ethyl trifluoromethanesulfonate represented by formula:

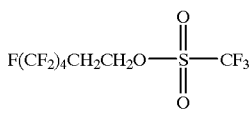

First, 26.4 g of 2-(perfluorobutyl)ethanol and 75 ml of dehydrated methylene chloride were put in a 200 ml flask provided with a calcium chloride tube, and cooled to 5° C. Then, 35.27 g of trifluoromethanesulfonic anhydride was dropped to the mixture while being stirred. Subsequently, 12.65 g of triethylamine was dropped to the mixture while being stirred. After the dropping, the resultant mixture was stirred for 24 hours. The resultant reaction solution was washed with 30 ml of water, further washed with 30 ml of 3% sulfuric acid, again washed with 30 ml of water, and dried with sodium sulfate. The solvent was then distilled off. The residue was distilled (b.p. 88° C. to 90° C./28 mmHg), to obtain 35.26 g (Y: 91.8%) of 2-(perfluorobutyl)ethyl trifluoromethanesulfonate. The purity of the resultant compound was 94.2% as measured by GC.

(14-b) Synthesis of compound 4-hydroxy-4'-[2-perfluorobutyl)ethyloxy]biphenyl represented by formula:

First, 3.0 g of 60% sodium hydride and 120 ml of dehydrated dimethoxyethane were put in an argon-replaced 300 ml flask. Then, 9.93 g of 4,4'-dihydroxybiphenyl was added while icing, and stirred at room temperature for two hours. The reaction solution was cooled again to −60° C., and 28.7 g of 2-(perfluorobutyl)ethyl trifluoromethanesulfonate was dropped into the reaction solution. After the resultant reaction solution was left to resume room temperature, it was stirred for 12 hours. After the reaction, dilute hydrochloric acid and benzene were added to the reaction solution to separate an organic layer. The organic layer was washed with a saturated brine and dried with sodium sulfate. The solvent was then distilled off. The residue was purified by silica gel column chromatography (eluent:benzene/ethyl acetate=9/1), and recrystallized from toluene to obtain 6.26 g (Y: 27.1%) of 4-hydroxy-4'-[2-(perfluorobutyl)ethyloxy]biphenyl. The purity of the resultant compound was 98.4% as measured by GC.

(14-c) Synthesis of compound (perfluorobutyl)ethyloxy]biphenyl-4-yl trifluoromethanesulfonate represented by formula:

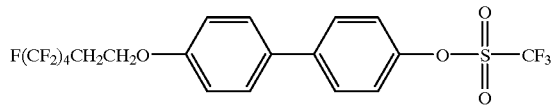

First, 5.00 g of 4-hydroxy-4'-[2-(perfluorobutyl)ethyloxy] biphenyl obtained from the synthesis (14-b) above and 100 ml of pyridine were put in a 200 ml flask provided with a calcium chloride tube, and cooled to −20° C. Then, 3.92 g of trifluoromethanesulfonic anhydride was dropped into the mixture while being stirred. After the dropping, the resultant mixture was stirred at 0° C. for 24 hours. The resultant reaction solution was poured into water and then extracted with ether. The resultant ether layer was washed with 5% hydrochloric acid, further washed with a saturated brine, and dried with sodium sulfate. The solvent was then distilled off. The residue was purified by silica gel column chromatography (eluent:toluene/hexane=1/4), to obtain 6.00 g (Y: 91.9%) of 4'-[2-(perfluorobutyl)ethyloxy]biphenyl-4-yl trifluoromethanesulfonate. The purity of the resultant compound was 100.0% as measured by GC.

(14-d) Synthesis of polymerizable compound 4'-[2-(perfluorobutyl)ethyloxy]-4-vinylbiphenyl represented by formula (N) above First, 6.00 g of 4'-[2-(perfluorobutyl)ethyloxy]biphenyl-4-yl trifluoromethanesulfonate obtained from the synthesis (14-c) above, 4.04 g of tributylvinyltin, 0.11 g of tris(dibenzylideneacetone)(chloroform)dipalladium(0), 0.05 g of tri(2-furyl)phosphine, 0.23 g of 2,6-di-tert-butyl-p-cresol, 1.35 g of lithium chloride, and 60 ml of dehydrated N-methylpirrolidone were put in an argon-replaced 100 ml flask, and stirred at 50° C. for eight hours. After the reaction, a saturated potassium fluoride aqueous solution and ether were added to the reaction solution and stirred for one hour. Insoluble material was then filtered off, and an organic layer was separated from the resultant filtrate. The organic layer was then washed with 5% ammonia water, further washed with a saturated brine, and dried with sodium sulfate. The solvent was then distilled off. The residue was purified by silica gel column chromatography (eluent: hexane/benzene= 9/1) and recrystallized from acetone, to obtain 2.72 g (Y: 57.8%) of 4'-[2-(perfluorobutyl)ethyloxy]-4-vinylbiphenyl. The purity of the resultant compound was 100.0% as measured by GC, 99.1% as measured by HPLC, and 1 spot as measured by TLC. The phase transfer temperature of the resultant compound was as follows.

crystal $\xrightarrow{138.7°\ C.}$ smectic B phase $\xrightarrow{168.0°\ C.}$ isotropic phase It was confirmed from the IR measurement result and Mass analysis that a molecular ion peak was recognized at 442 and that the resultant substance was the compound represented by formula (N) above in consideration of the materials used.

SYNTHESIS EXAMPLE 15

Synthesis of Polymerizable Compound (R)-4-(1-methylpentyloxy)-4'-vinylbiphenyl Represented by Formula (O)

formula (O)

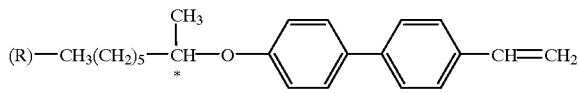

(15-a) Synthesis of compound (R)-4'-(1-methylheptyloxy) biphenyl-4-yl trifluoromethanesulfonate represented by formula:

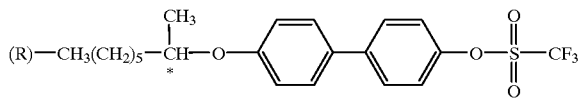

First, 5.00 g of (R)-4'-(1-methylheptyloxy)-4-hydroxybiphenyl and 25 ml of pyridine were put in a 100 ml flask provided with a calcium chloride tube, and cooled to −20° C. Then, 5.25 g of trifluoromethanesulfonic anhydride was dropped into the mixture while being stirred. After the dropping, the resultant mixture was stirred at 0° C. for 24 hours. The resultant reaction solution was poured into water and then extracted with ether. The resultant ether layer was washed with 5% hydrochloric acid, further washed with a saturated brine, and dried with sodium sulfate. The solvent was then distilled off. The residue was purified by silica gel column chromatography (eluent:hexane), to obtain 7.04 g (Y: 97.3%) of (R)-4'-(1-methylheptyloxy)biphenyl-4-yl trifluoromethanesulfonate. The purity of the resultant compound was 99.5% as measured by GC.

(15-b) Synthesis of polymerizable compound (R)-4-(1-methylheptyloxy)-4'-vinylbiphenyl represented by formula (O) above First, 7.04 g of (R)-4'-(1-methylheptyloxy)biphenyl-4-yl trifluoromethanesulfonate obtained from the synthesis (15-a) above, 6.22 g of tributylvinyltin, 0.17 g of tris (dibenzylideneacetone)(chloroform)dipalladium(0), 0.15 g of tri(2-furyl)phosphine, 2.08 g of lithium chloride, several pieces of crystal of 2,6-di-tert-butyl-p-cresol, and 33 ml of dehydrated N-methylpirrolidone were put in an argon-replaced 100 ml flask, and stirred at 50° C. for five hours. After the reaction, a saturated potassium fluoride aqueous solution and hexane were added to the reaction solution and stirred for one hour. Insoluble material was then filtered off, and an organic layer was separated from the resultant filtrate. The organic layer was then washed with 5% ammonia water, further washed with a saturated brine, and dried with sodium sulfate. The solvent was then distilled off. The residue was purified by silica gel column chromatography (eluent:hexane) and recrystallized from hexane, to obtain 3.30 g (Y: 65.2%) of (R)-4-(1-methylheptyloxy)-4'-vinylbiphenyl. The purity of the resultant compound was 99.9% as measured by GC, 100.0% as measured by HPLC, and 1 spot as measured by TLC. M.p. was 80.6° C.

It was confirmed from the IR measurement result and Mass analysis that a molecular ion peak was recognized at 308 and that the resultant substance was the compound represented by formula (O) above in consideration of the materials used.

Hereinbelow, an embodiment of the liquid crystal display (LCD) device according to the present invention is described.

Figure 8A:
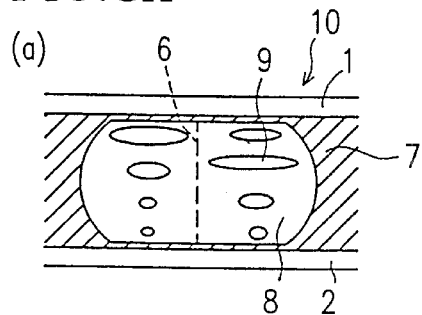
FIGS. 8A and 8B respectively show schematic cross-sectional views of an LCD device according to one aspect of the present invention and a conventional TN type LCD device, illustrating the relationship between a change in the orientation of liquid crystal molecules and the viewing angle characteristic in accordance with application of a voltage.
Figure 8A:
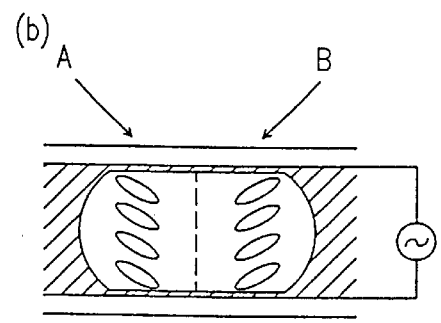
Figure 8A:
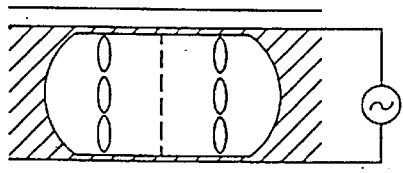
Figure 8B:
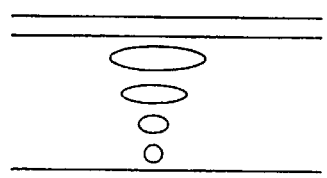
Figure 8B:
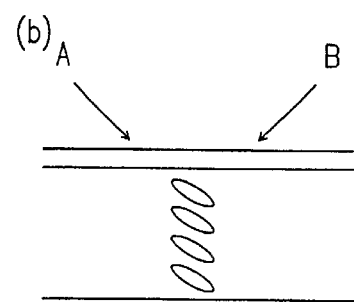
Figure 8B:
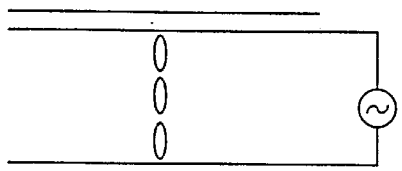

As shown in FIG. 8A, an LCD device 10 according to the present invention includes a pair of substrates 1 and 2 and a liquid crystal layer interposed between the substrates 1 and 2. The liquid crystal layer contains a plurality of liquid crystal domains 8 each substantially surrounded by a polymer wall 7 which is made of a photopolymerizable resin material. In this embodiment, the liquid crystal domains 8 are substantially surrounded by the substrates 1 and 2 and the polymer wall 7. The substrates 1 and 2 each has a transparent electrode (not shown) in a desired pattern on a surface thereof in the vicinity of the liquid crystal layer. Liquid crystal molecules 9 in the liquid crystal domain 8 are twisted in an axially symmetrical state. In this embodiment, the twist angle was set to be about 90 degrees.

In this embodiment of the present invention, the LCD device 10 is of transmission-type. In the case of a reflection-type LCD device, one of the substrates can be formed of an opaque substrate such as a semiconductor substrate.

In this embodiment, one liquid crystal domain is formed for each of a plurality of pixel areas. In the case where the pixels have different pitches in perpendicular directions to each other, a plurality of liquid crystal domains can be formed for each pixel area. In such a case also, the liquid crystal domains are allowed to be arranged spatially regularly.

Hereinbelow, methods for producing the LCD device 10 according to the present invention is described.

Examples 1 to 3

Production of LCD Device Using Polymerizable Compound by Mask Pattern Exposure

Two glass substrates 1 and 2 each having a thickness of about 1.1 mm and having thereon a transparent electrode having a thickness of 50 nm and formed of ITO (mixture of indium oxide and tin oxide) were provided. The glass substrates 1 and 2 were combined together while a gap therebetween was maintained as a cell thickness by spacers (not shown) having a diameter of about 5 μm, to form a liquid crystal cell.

Figure 9:
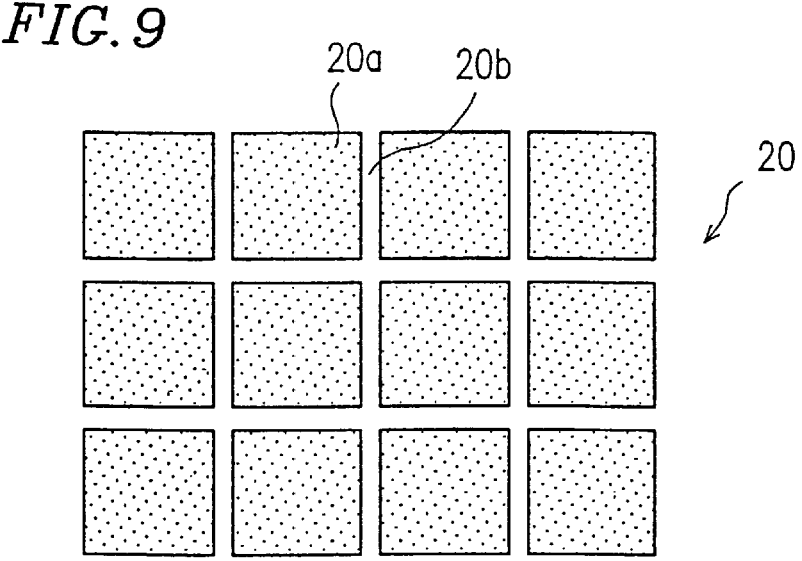
FIG. 9 is a schematic plan view of a photomask used in Examples 1 to 3 according to one aspect of the present invention.

A photomask 20 shown in FIG. 9 having light-blocking areas 20a and light-transmissive areas 20b was put on the liquid crystal cell. A precursor mixture was injected into the resultant cell by capillary injection. The precursor mixture was obtained by uniformly mixing a polymerizable resin material, a liquid crystal material, and a photoinitiator. Used as the polymerizable resin material was a mixture of 0.65 g of a isobornyl acrylate, 0.15 g of 1,4-butanediole acrylate, and 0.20 g of a polymerizable compound X represented in Table 1 below. Used as the liquid crystal material was 13.3 g of ZLI-4792 (produced by Merck & Co. Inc.; Δn=0.094). Used as the photoinitiator was 0.04 g of Irgacure 651.

TABLE 1

| Polymerizable compound X | Example No. |
|---|---|
| 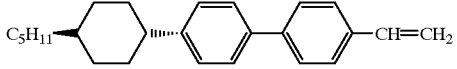 | 1 |
| 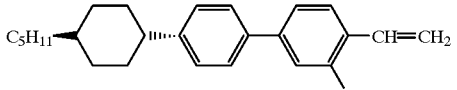 | 2 |
| 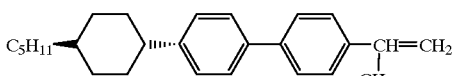 | 3 |

Thereafter, the liquid crystal cell was irradiated with ultraviolet light from a high-pressure mercury lamp through the photomask 20 at 100° C. for eight minutes while applying a voltage having an amplitude of 3 V between the transparent electrodes. The cell was put below the mercury lamp at 10 mW/cm², so that collimated light rays were obtained. Thus, the precursor mixture in the cell was irradiated by the ultraviolet light having an intensity distribution of a spatially regular pattern. The temperature of the light irradiation is preferably equal to or higher than the temperature at which a mixture is soluble each other and also equal to or lower than the $T_{N-I}$ point of the liquid crystal phase after phase separation. The orientation of the liquid crystal molecules is stabilized by applying a voltage to the liquid crystal phase while the liquid crystal phase is formed by photopolymerization-induced phase separation.

While the voltage was applied, the cell was gradually cooled (10° C./hour) to 25° C. (the liquid crystal material was in a nematic state), and the entire surface of the cell was irradiated with ultraviolet light for three minutes continuously without a photomask, thereby further curing the resin in the cell.

Figure 10:
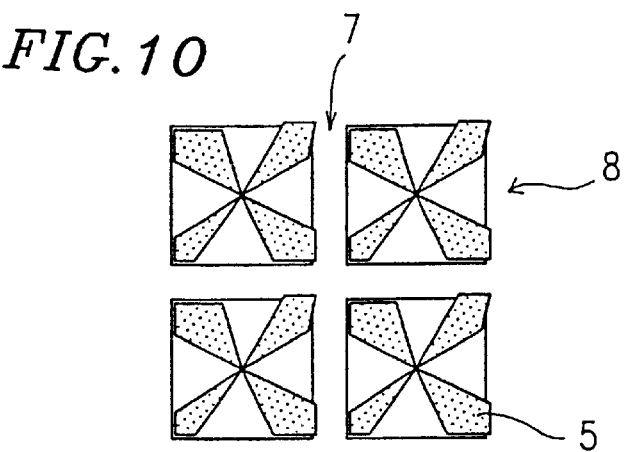
FIG. 10 schematically shows an LCD device in Examples 1 to 3 according to one aspect of the present invention observed by a polarization microscope.

The resultant liquid crystal panel was observed by a polarization microscope and confirmed to have the polymer wall 7 and the liquid crystal domains 8 as shown in FIG. 10, substantially reflecting the pattern of the photomask 20. Based on a radial light extinction pattern 5 observed in the liquid crystal domains 8, it was confirmed that the liquid crystal molecules were oriented in an axially symmetric state with respect to an axis in the vicinity of the center of the liquid crystal domains 8. At such an axially symmetric orientation, liquid crystal molecules having a molecule axis parallel to the polarizing axis of the polarizer and liquid crystal molecules having a molecule axis tilting with respect to the polarizing axis of the polarizer are continuously existent. As a result, a radial light extinction pattern is observed.

Next, polarizers were put on two outer surfaces of the liquid crystal panel so that the polarizing axes of the polarizers were perpendicular to each other.

The characteristics of the LCD devices in Examples 1 and 2 are shown in Table 2 below.

The evaluation criteria of the LCD devices were as follows.

Electrooptical characteristics: The voltage vs. transmittance characteristic was measured by a liquid crystal characteristic evaluation system LCD-5000 (produced by Otsuka Denshi Kabushiki Kaisha). As a reference, a cell having polarizers on two outer surfaces of the above-described glass substrates in a parallel-Nicols arrangement was used.

Response time (response speed): The time period required for the relative transmittance to change by 90% was measured while changing the applied voltage between 0 V to 5 V. The evaluation was conducted by the sum of $\tau_r + \tau_d$ (ms), where $\tau_r$ is the time period required for the transmittance to rise (ms) and $\tau_d$ is the time period required for the transmittance to fall (ms).

$T_{N-I}$ point in the liquid crystal domain: The temperature at which an isotropic liquid crystal phase appears in the nematic phase was observed by a polarization microscope at the measurement point at the center of the panel while increasing the temperature of the panel at the rate of 0.1° C./min. The $T_{N-I}$ distribution in the liquid crystal domain is represented by an absolute value of the difference between the $T_{N-I}$ temperatures at an injection opening and a fixed point opposed to the injection opening.

Voltage retaining ratio: After a pulse voltage having a selective pulse width of 10 sec. and an amplitude of 5 V was applied, the ratio of the voltage retained during 16.7 milliseconds was measured. The measurement temperature was 60° C.

Residual DC voltage: A voltage of DC 10 V was applied for one hour and shortcircuiting occurred for one second by a capacitor dielectric absorption method. Ten minutes later, the voltage was measured. The measurement temperature was 60° C.

Panel afterimage: A fixed pattern was displayed on the liquid crystal panel at 60° C. for one hour, and then the voltage was removed (shortcircuited) to observe the degree of an afterimage on the panel.

TABLE 2

| Example No. | 1 | 2 | 4 | 5 | 7 | 8 | Comparative example 1 | Comparative example 2 | Comparative example 3 | Comparative example 4 |
|---|---|---|---|---|---|---|---|---|---|---|
| Transmittance at black display (%) | 1.2 | 0.9 | 0.6 | 0.7 | 0.3 | 0.2 | 0.7 | 2.2 | 0.6 | 0.6 |
| Inversion at gray-scal display*[1] | ○ | ○ | ○ | ○ | ○ | ○ | X | Δ | ○ | ○ |
| Response speed (10V; ms) | 58 | 56 | 50 | 53 | 51 | 53 | 34 | 330 | 220 | 240 |
| Pixel $T_{N-I}$ temperature (° C.) | 78 | 79 | 80 | 80 | 85 | 87 | 83 | 79 | 76 | 75 |

TABLE 2-continued

| Example No. | 1 | 2 | 4 | 5 | 7 | 8 | Comparative example 1 | Comparative example 2 | Comparative example 3 | Comparative example 4 |
|---|---|---|---|---|---|---|---|---|---|---|
| Voltage retaining ratio (%) | 95 | 96 | 96 | 95 | 95 | 95 | 98 | 93 | 94 | 94 |
| Residual DC voltage (mV) | 100 | 80 | 45 | 65 | 50 | 70 | 65 | 180 | 330 | 250 |
| Panel after image *2) | b | b | a | b | a | b | b | c | d | c |

As is seen from Table 2 above, no inversion phenomenon was observed in the LCD devices in Examples 1 and 2. Such an inversion phenomenon was observed in LCD devices in Comparative examples 1 and 2which is described hereinbelow. No increase in the transmittance in a direction of a large viewing angle was observed in Examples 1 and 2. No unevenness of the display in a gray-scale display was observed, either, in Examples 1 and 2.

The response speed, the residual DC voltage, and the panel afterimage evaluation were all relatively good compared with those in Comparative examples 2 to 4 which are described hereinbelow.

In the LCD devices in Examples 2 and 3, generation of disclination lines in the liquid crystal domains was completely suppressed. In the LCD device in Example 1, a very small amount of disclination lines were generated.

Examples 4 to 6

Production of LCD Device Using Polymerizable Compound by Insulator Pattern Exposure In Examples 4 to 6, an LCD device was produced in the same manner as in Examples 1 to 3 except that a patterning wall was provided in an area of the liquid crystal layer in which the polymer wall was to be formed, and the liquid crystal cell was irradiated with ultraviolet light without using a photomask.

Figure 11:
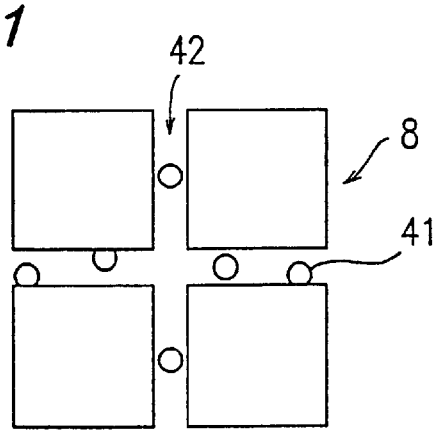
FIG. 11 is schematic plan view of a substrate of an LCD device in Examples 4 to 6 according to one aspect of the present invention, illustrating a patterning wall.

Two glass substrates each having a thickness of about 1.1 mm and having thereon a transparent electrode formed of ITO were provided. As shown in FIG. 11, a patterning wall 42 containing spacers 41 having a diameter of about 5 m was formed on one of the substrates to a height of about 2.7 μm. In this example, the patterning wall 42 was formed of a negative photoresist OMR83 (produced by Tokyo Ohka Kabushiki Kaisha). The two glass substrates were combined together by a seal resin. Thus, a liquid crystal cell was produced.

A precursor mixture was injected into the cell by vacuum injection. The precursor mixture was obtained by uniformly mixing a photopolymerizable resin material, a liquid crystal material, and an photoinitiator. Used as the photopolymerizable resin material was a mixture of 0.65 g of isobornyl acrylate, 0.15 g of neopentyl diacrylate, and 0.20 g of a polymerizable compound represented in Table 3 below. Used as the liquid crystal material was 13.3 g of ZLI-4792 (produced by Merck & Co. Inc.; Δn=0.094). Used as the photoinitiator was 0.04 g of Irgacure 651.

TABLE 3

| Polymerizable compound Y | Example No. |
|---|---|
| 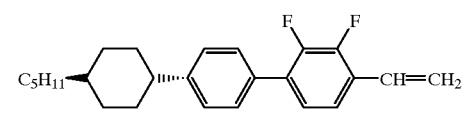 | 4 |
| 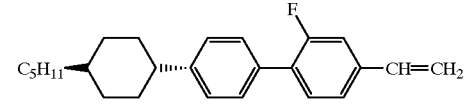 | 5 |
| 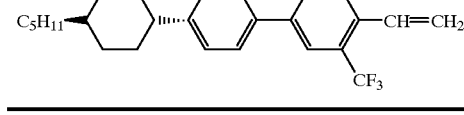 | 6 |

After the orientation of the liquid crystal molecules was controlled by phase separation, the liquid crystal molecules were oriented in an axially symmetrical state in liquid crystal domains each surrounded by the patterning wall 42. The precursor mixture in the cell was irradiated by ultraviolet light at room temperature for 15 minutes below a high-pressure mercury lamp at 6 mW/cm². In order to completely cure the resin, irradiation with ultraviolet light was performed for another 10 minutes continuously using the same lamp as a light source.

The resultant liquid crystal panel was observed with a polarization microscope to confirm that the liquid crystal molecules were oriented in an axial symmetrical state as in Examples 1 to 3. This was confirmed in the following manner. The resultant liquid crystal panel was rotated while two polarizers of which polarizing axes were perpendicular to each other were fixed. If the schlieren pattern of the liquid crystal domains is unchanged while the surrounding polymer wall rotates, then the axial symmetric orientation of the liquid crystal molecules is confirmed.

Next, polarizers were put on two outer surfaces of the liquid crystal panel so that the polarizing axes of the polarizers were perpendicular to each other. The characteristics of the resultant LCD devices in Examples 4 and 5 are shown in Table 2 above.

As is seen from Table 2, no inversion phenomenon was observed in the LCD devices in Examples 4 and 5. Such an inversion phenomenon was observed in LCD devices in Comparative examples 1 and 2 which are described hereinbelow. No increase in the transmittance in a direction of a large viewing angle was observed in Examples 4 and 5. No unevenness of the display in a gray-scale display was observed, either, in Examples 4 and 5.

The response speed, the residual DC voltage, and the panel afterimage evaluation were all relatively good compared with those in Comparative examples 2 to 4. The display state at black display was also relatively good compared with those in Comparative examples 2 to 4.

Examples 7 and 8

In Examples 7 and 8, an LCD device was produced in the following manner.

Figure 12A:
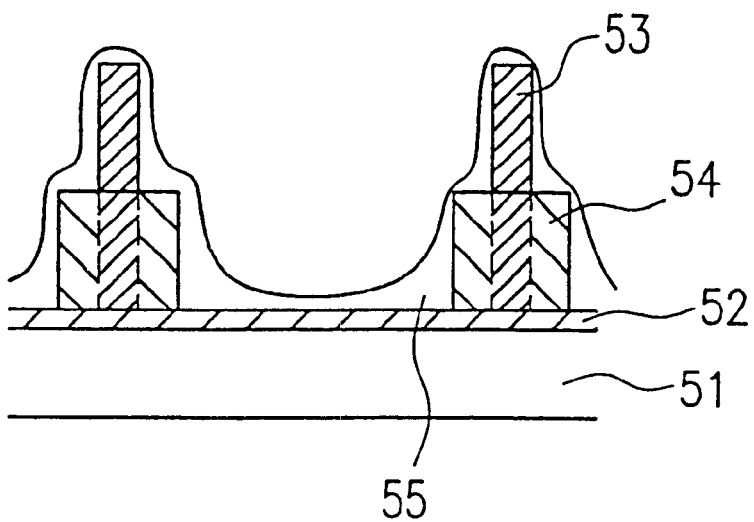
FIG. 12A is a schematic cross-sectional view of a substrate of an LCD device in Examples 4 to 6 according to one aspect of the present invention.
Figure 12B:
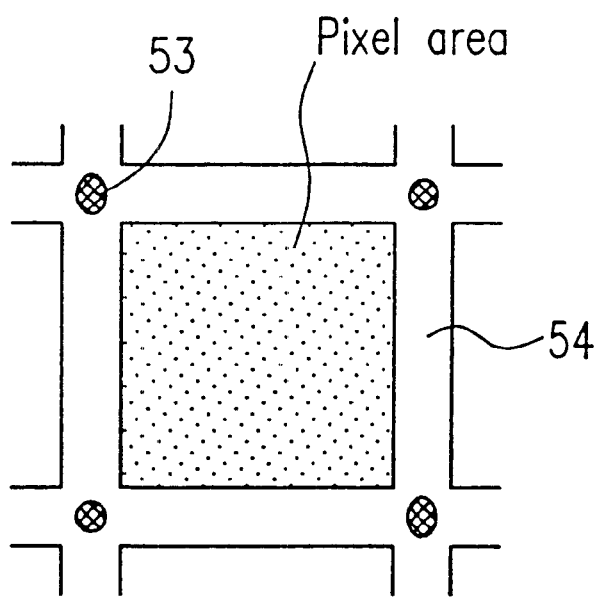
FIG. 12B is a schematic plan view of the substrate shown in FIG. 12A.

As shown in FIGS. 12A, a transparent electrode 52 formed of ITO was formed on a glass substrate 51. Column-like spacers 53 having a thickness of about 5.3 μm were formed on the glass substrate 51 by photolithography using photosensitive polyimide. The spacers 53 were formed in areas corresponding to areas excluded from the pixel areas as shown in FIG. 12B. Next, a patterning wall 54 having a thickness of about 3 m was formed so as to surround the pixel areas. The patterning wall 54 was formed of a negative photoresist OMR83 (produced by Tokyo Ohka Kabushiki Kaisha). Then, a liquid crystal alignment layer 55 was formed of JALS-204 (produced by Japan Synthetic Rubber Co.) so as to cover the spacers 53 and the patterning wall 54. Although not shown, the same type of liquid crystal alignment layer was formed on a transparent electrode of the other glass substrate. The two glass substrates were combined together to produce a liquid crystal cell.

A precursor mixture of a photopolymerizable resin material, a liquid crystal material, and a photoinitiator was injected into the cell by vacuum injection. Used as the liquid crystal material was an Nn liquid crystal material ($\Delta\epsilon$: –3.5; $\Delta$n: 0.08; $T_{N-1}$: 90° C.; cell gap: 5.4 m; set to have a twist angle of 90 degrees using a chiral agent. The twist angle is inherent to liquid crystal materials). Used as the photopolymerizable resin material was 0.8 wt. % of polymerizable compound Z represented in Table 4 below. Used as the photoinitiator was 0.15 wt % of Irgacure 651.

TABLE 4

| Polymerizable compound Z | Example No. |
| --- | --- |
| C$_3$H$_7$—⟨⟩—⟨⟩—⟨F,F⟩—CH=CH$_2$ | 7 |
| n-C$_4$F$_9$—⟨⟩—⟨⟩—CH=CH$_2$ | 8 |

After the injection, the liquid crystal molecules were oriented in an axially symmetrical state by applying a voltage of 5 V. The domains in which the liquid crystal molecules were oriented in an axially symmetrical state had a central axis at the center of the pixel area and formed within the patterning wall 54. Then, irradiation with ultraviolet light of 365 nm was performed at room temperature for 10 minutes at 6 mW/cm$^2$ while applying a voltage which is 0.5 V higher than the threshold voltage, thereby curing the photopolymerizable resin material in the mixture. Thus, the axial symmetric orientation in the liquid crystal domains was stabilized.

Next, polarizers were put on two outer surfaces of the liquid crystal panel so that the polarizing axes of the polarizers were perpendicular to each other. The characteristics of the resultant LCD devices in Examples 7 and 8 are shown in Table 2 above.

As is seen from Table 2, no inversion phenomenon was observed in the LCD devices in Examples 7 and 8. Such an inversion phenomenon was observed in LCD devices in Comparative examples 1 and 2 which will be described hereinbelow.

The response speed, the residual DC voltage, and the panel afterimage evaluation were relatively good compared with those in Comparative examples 2 to 4 which are described hereinbelow. The display state at black display was also relatively good compared with those in Comparative examples 2 to 4.

Comparative Example 1

TN-LCD

Glass substrates each having thereon a transparent electrode formed of ITO similar to that in Example 1 were provided. On each of the glass substrates, a polyimide insulating film AL4552 as an alignment film was applied and treated by rubbing with a nylon cloth. The resultant glass substrates were disposed so that the rubbing directions were perpendicular to each other, and combined together with spacers having an average grain diameter of 5 μm.

A liquid crystal material ZLI-4792 (containing 0.3 wt. % of S-811) similar to that used in Example 1 was injected into the resultant liquid crystal cell.

Next, polarizers were put on two outer surfaces of the liquid crystal panel so that the polarizing axes of the polarizers were parallel to the rubbing direction of the corresponding alignment layer and perpendicular to each other. The characteristics of the resultant LCD device were evaluated, and the results are as shown in Table 2 above.

As is seen from Table 2, in the LCD device in Comparative example 1, an inversion phenomenon was observed at gray-scale display.

Comparative Example 2

The photomask 20 shown in FIG. 9 was put on the liquid crystal cell produced in Example 1. A precursor mixture was injected into the resultant cell by capillary injection. The precursor mixture was obtained by uniformly mixing a polymerizable resin material, a photoinitiator, and a liquid crystal material. Used as the photopolymerizable resin material was a mixture of 0.75 g of stearyl acrylate, 0.15 g of 1,4-butanediol, and 0.10 g of t-buthoxystylene. Used as the photoinitiator was 0.04 g of Irgacure 651. Used as the liquid crystal material was 13.3 g of ZLI-4792 (produced by Merck & Co. Inc.; n=0. 094).

Thereafter, as in Example 1, the surface of the liquid crystal cell where the photomask 20 was formed was irradiated with ultraviolet light to allow photopolymerization phase separation to proceed while a voltage is applied to the cell.

Polarizers were put on two outer surfaces of the liquid crystal panel so that the polarizing axes of the polarizers were in a crossed-Nicols arrangement. The characteristics of the resultant LCD device were evaluated, and the results are as shown in Table 2 above.

As is seen from Table 2, in the LCD device in Comparative example 2, an inversion phenomenon was observed at gray-scale display. The phase separation of the liquid crystal material from the polymer was insufficient, so that some of the resin material was observed mixed in the liquid crystal domains. The display characteristics were insufficient since disclination lines were generated when a voltage was applied. The transmittance at the application of a voltage of 10 V was 2.2%. Since this value is larger than that of the LCD device in Example 4, for example, this low transmittance is considered to be mainly caused by the generation of disclination lines.

Comparative Examples 3 and 4

A patterning wall 42(a negative photoresist OMR83 produced by Tokyo Ohka Kabushiki Kaisha) containing spacers 41 having a diameter of 5 µm was formed on one of a pair of substrates, as in Example 4. This substrate and the other substrate were combined together with a seal resin therebetween to form a liquid crystal cell. A precursor mixture was injected into the resultant cell by vacuum injection under a decompressed condition. The precursor mixture was obtained by uniformly mixing a polymerizable resin material, a photoinitiator, and a liquid crystal material. Used as the polymerizable resin material was a mixture of 0.65 g of isobornyl acrylate, 0.15 g of neopentyl diacrylate, 0.10 g of p-methylstylene, and 0.10 g of a polymerizable compound represented in Table 5 below. Used as the photoinitiator was 0.04 g of Irgacure 651. Used as the liquid crystal material was 13.3 g of ZLI-4792 (produced by Merck & Co. Inc.; Δn=0. 094).

TABLE 5

| Polymerizable compound A | Comparative No. |
|---|---|
| $CH_2=CHCOO(CH_2)_6O$—[structure with two fluorinated phenyl rings] | 3 |
| $CH_2=CHCOO(CH_2)_8O$—[structure with two phenyl rings, one fluorinated] | 4 |

Thereafter, as in Example 4, the liquid crystal cell was irradiated with ultraviolet light to allow photopolymerization phase separation to proceed while a voltage is applied to the cell.

Polarizers were put on two outer surfaces of the liquid crystal panel so that the polarizing axes of the polarizers were in a crossed-Nicols arrangement. The characteristics of the resultant LCD device were evaluated, and the results are as shown in Table 2 above.

As is seen from Table 2, in the LCD devices in Comparative examples 3 and 4, it was observed with a polarization microscope that the generation of disclination lines at the application of a voltage had been suppressed. This is due to the existence of a polymerizable compound having a liquid crystal-like structure in molecules in the polymerizable resin material. As a result, the light transmittance at black display was 0.6%, exhibiting a comparatively good black display state.

However, when compared with Examples 1 to 8, the LCD devices in Comparative examples 3 and 4 were insufficient in the characteristics including the response speed ($\tau_r+\tau_d$), the residual DC voltage, and the panel afterimage evaluation. This indicates that the LCD device using a polymerizable compound according to the present invention is superior to these comparative examples, and that the problems of the conventional LCD devices can be minimized and solved by using the polymerizable compound according to the present invention.

Example 9

TN Mode

Figure 13:
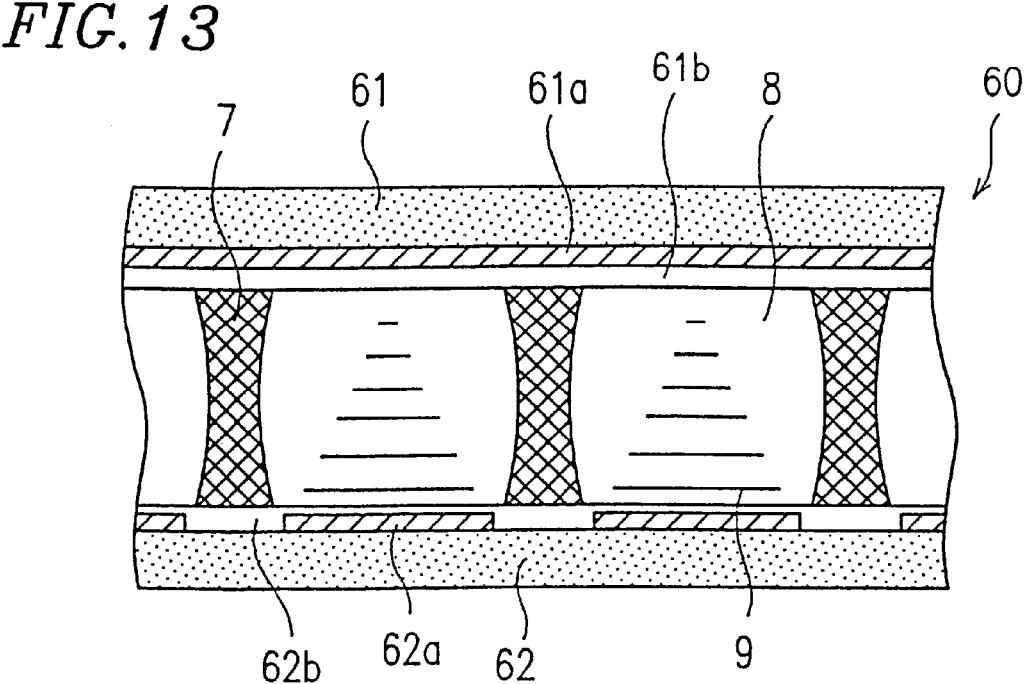
FIG. 13 is a schematic cross-sectional view of an LCD device in Example 9 according to one aspect of the present invention.

FIG. 13 is a cross-sectional view of an LCD device 60 in Example 4 according to the present invention. The LCD device 60 has substantially the same structure as the LCD device 10 in Example 1 except that the liquid crystal molecules 9 in the liquid crystal domains are oriented in a TN state. In order to obtain the TN orientation, alignment layers 61b and 62b are provided respectively on glass substrates 61 and 62 in the vicinity of a liquid crystal layer interposed between the substrates 61 and 62. The alignment layers 61b and 62b are treated by rubbing in a prescribed direction.

The LCD device 60 was produced in the following manner.

The glass substrates 61 and 62 respectively having thereon transparent electrodes 61a and 62a formed of ITO were provided. On each of the glass substrates 61 and 62, a liquid crystal alignment layer AL4552 (produced by Japan Synthetic Rubber Co.) was applied and treated by rubbing with a nylon cloth. The two glass substrates 61 and 62 with the alignment layers were combined so that the rubbing directions were perpendicular to each other, thereby producing a liquid crystal cell.

A precursor mixture of the same photopolymerizable resin material as that used in Example 4, a photoinitiator, and a liquid crystal material was injected into the cell by vacuum injection. ZLI-4792 (produced by Merck & Co., Inc.) was used as the liquid crystal material, which, in this example, was adjusted to have a chiral pitch of 80 m.

A photomask 20 (FIG. 9) having light-blocking areas 20a and light-transmissive areas 20b was put on the liquid crystal cell, and a TN mode liquid crystal panel including liquid crystal domains 8 each surrounded by the polymer wall 7 was produced in the same manner as in Example 1.

Next, polarizers were put on two outer surfaces of the liquid crystal panel so that the polarizing axes of the polarizers were parallel to the rubbing direction of the corresponding alignment layer and perpendicular to each other. Thus, the LCD device 60 was obtained.

In LCD device 60, the liquid crystal molecules 9 in each liquid crystal domain 8 were oriented in a TN state and uniformly. The display characteristics did not change when the display surface was pushed by a pen.

It has been confirmed that using the polymerizable compound according to the present invention improves the orientation stability of the liquid crystal layer and the uniformity of the orientation of the liquid crystal molecules. As a result, the display characteristics of the LCD device are enhanced.

The above effects can also be obtained by LCD devices of display modes such as the STN mode, the SSFLC mode, and the ECB mode in which uniform orientation of liquid crystal molecules is regulated in various ways.

Thus, as described above, a specific polymerizable compound is used in the LCD device including a liquid crystal layer having liquid crystal domains surrounded by a polymer wall or a wall structure. The polymerizable compound contains a methogen group having a structure which resembles that of a liquid crystal compound and a styrene or -methylstyrene polymerizable functional group coupled with each other. By using such a polymerizable compound, the orientation of liquid crystal molecules can be stabilized and generation of disclination lines can be suppressed.

Moreover, the interaction at the interface of the liquid crystal molecules and the polymer wall can be adjusted. This minimizes problems caused by a decrease of the response speed, a decrease of the threshold characteristic and sharpness in the voltage vs. transmittance characteristics, and the like, as well as a printing afterimage phenomenon caused by an excessively strong memory effect at the interface.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A polymerizable compound represented by general formula (I):

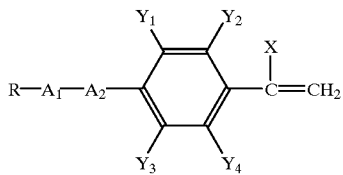

(I)

where R is H, R', R'O, R'COO, or R'OCO, R' is a linear or branched alkyl group or alkenyl group having 1 to about 15 carbon atoms; $A_1$ and $A_2$ are independently a cyclohexane ring or a benzene ring which may include a substituent represented by formula (II) below; X is H or $CH_3$; and $Y_1$, $Y_2$, $Y_3$ and $Y_4$ are independently H, F, Cl, $CH_3$, $CH_3O$, $CF_3$, or $CF_3O$ wherein at least two of $Y_1$, $Y_2$, $Y_3$, and $Y_4$ is H and, if both $A_1$ and $A_2$ are cyclohexane rings, at least one of $Y_1$, $Y_2$, $Y_3$, and $Y_4$ is not H, and if $A_1$ is a cyclohexane ring and $A_2$ is a benzene ring, at least one of $Y_1$, $Y_2$, $Y_3$ and $Y_4$ is not H:

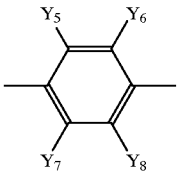

(II)

where $Y_5$, $Y_6$, $Y_7$, and $Y_8$ are independently H, F, Cl, $CH_3$, $CH_3O$, $CF_3$, or $CF_3O$, at least two of $Y_5$, $Y_6$, $Y_7$, and $Y_8$ are H.

2. A polymerizable compound according to claim 1, wherein in general formula (I) $A_1$ is a cyclohexane ring and $A_2$ is a benzene ring.

3. A polymerizable compound according to claim 1, wherein in general formula (I) both $A_1$ and $A_2$ are cyclohexane rings.

4. A polymerizable compound represented by general formula (III):

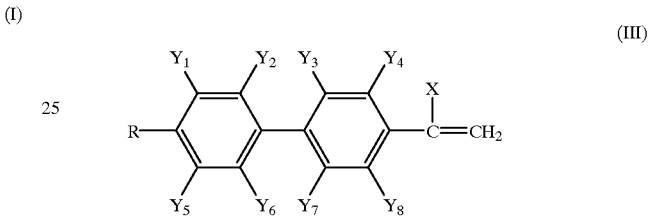

(III)

where R is H, F, or a linear or branched alkyl group or alkoxy group having 1 to about 15 carbon atoms of which an arbitrary hydrogen atom may be substituted by a fluorine atom; $Y_1$, $Y_2$, $Y_3$, $Y_4$, $Y_5$, $Y_6$, $Y_7$, and $Y_8$ are independently H or F X is H or $CH_3$ wherein at least one of $Y_1$, $Y_2$, $Y_3$, $Y_4$, $Y_5$, $Y_6$, $Y_7$, and $Y_8$ is F if R is a linear alkyl group of which an arbitrary hydrogen atom is not substituted by a fluorine atom.

5. A polymerizable resin composition including a polymerizable resin material containing the polymerizable compound according to claims 1 or 4 and an initiator mixed with each other.

* * * * *